(12) United States Patent
Golway et al.

(10) Patent No.: US 10,392,595 B2
(45) Date of Patent: Aug. 27, 2019

(54) VASCULARIZED IN VITRO PERFUSION DEVICES, METHODS OF FABRICATING, AND APPLICATIONS THEREOF

(71) Applicant: Advanced Solutions Life Sciences, LLC, Louisville, KY (US)

(72) Inventors: Michael W. Golway, Louisville, KY (US); James B. Hoying, Louisville, KY (US)

(73) Assignee: Advanced Solutions Life Sciences, LLC, Louisville, KY (US)

( * ) Notice: Subject to any disclaimer, the term of this patent is extended or adjusted under 35 U.S.C. 154(b) by 21 days.

(21) Appl. No.: 15/202,675

(22) Filed: Jul. 6, 2016

(65) Prior Publication Data
US 2017/0009194 A1 Jan. 12, 2017

Related U.S. Application Data

(60) Provisional application No. 62/188,803, filed on Jul. 6, 2015, provisional application No. 62/279,019, filed on Jan. 15, 2016.

(51) Int. Cl.
| | | |
|---|---|---|
| C12N 5/00 | (2006.01) | |
| C12M 1/00 | (2006.01) | |
| C12M 1/12 | (2006.01) | |
| C12M 3/06 | (2006.01) | |
| G01N 33/50 | (2006.01) | |

(52) U.S. Cl.
CPC ............ *C12M 29/10* (2013.01); *C12M 23/16* (2013.01); *C12M 25/14* (2013.01); *G01N 33/502* (2013.01); *G01N 33/5064* (2013.01)

(58) Field of Classification Search
CPC ..... A61L 27/507; A61L 27/3808; C12N 5/00; C12M 29/10; C12M 25/14; C12M 23/16
See application file for complete search history.

(56) References Cited

U.S. PATENT DOCUMENTS

| | | | |
|---|---|---|---|
| 7,029,838 | B2 | 4/2006 | Williams et al. |
| 7,052,829 | B2 | 5/2006 | Williams et al. |
| 2006/0018838 | A1 | 1/2006 | George et al. |
| 2009/0181200 | A1* | 7/2009 | Borenstein .......... B81C 1/00119 428/36.9 |
| 2010/0075293 | A1 | 3/2010 | Chang et al. |
| 2013/0004469 | A1 | 1/2013 | Glazier et al. |
| 2015/0231182 | A1 | 8/2015 | Boyd et al. |

FOREIGN PATENT DOCUMENTS

| | | |
|---|---|---|
| WO | 2015069619 A1 | 5/2015 |
| WO | 2016141137 A1 | 9/2016 |

OTHER PUBLICATIONS

International Search Report and Written Opinion of corresponding PCT Application No. PCT/US2016/041034 dated Sep. 16, 2016.
Benjamin R. Shepherd et al, "Rapid Perfusion and Network Remodeling in a Microvascular Construct After Implantation," Arterioscler Thromb Vasc Biol., May 2004; pp. 898-904.
Sara S. Nunes et al, "Implanted Microvessels Progress through Distinct Neovascularization Phenotypes," NIH Public Access Author Transcript; Microvasc Res. Jan. 2010; 79(1); pp. 1-21.
Xioafang Chen et al, "Prevascularization of a Fibrin-Based Tissue Construct Accelerates the Formation of Functional Anastomosis with Host Vasculature," Tissue Engineering, Part A, vol. 15, No. 6, 2009, pp. 1363-1371.
Carlos S. Chang et al, "Direct-write Bioprinting Three-Dimensional Biohybrid Systems for Future Regenerative Therapies," NIH Public Access Author Manuscript; J Biomed Mater Res B Appl Biomater, Jul. 2011, 98 (1); pp. 160-170.
Amanda J. Leblanc et al, "Microvascular Repair: Post-Angiogenesis Vascular Dynamics," NIH Public Access Author Manuscript; Microcirculatoin, Nov. 2012, 19(8); pp. 1-32.
John P. Morgan et al, "Formation of Microvascular Networks In Vitro," Nature Protocols, 2013, vol. 8, No. 9, pp. 1820-1836.
Ritika R. Chaturvedi et al, "Patterning Vascular Networks In Vivo for Tissue Engineering Applications," Tissue Engineering, Part C, vol. 21, No. 5, 2015. pp. 509-517.
Monica Moya et al, "An integrated in vitro model of perfused tumor and cardiac tissue," Stem Cell Research & Therapy, 2013, 4 (Suppl 1): N; pp. 1-6.
Vivian K. Lee et al, "Creating perfused functional vascular channels using 3D bio-printing technology," Biomaterials 35 (2014); 8092-8102.
European Search Report relating of Corresponding PCT Application No. PCT/US2016041034 dated Sep. 24, 2018.
Vollert, Ingra, et al., "In-Vitro Perfusion of Engineered Heart Tissue Through Endothelialized Channels", Tissue Engineering, Part A. Oct. 25, 2013.
Chang, Carlos, "Angiogenesis in a Microvascular Construct for Transplantation Depends on the Method of Chamber Circulation", Tissue Engineering, Part A, vol. 16, Dec. 31, 2010.
Morgan, John P. et al., "Formation of Microvascular Networks In Vitro", Nature Protocols, Nature Publishing Group, GB, vol. 8, No. 9, Aug. 31, 2013.
Chang, Carlos, "Determinants of Microvascular Network Technologies in Implanted Neovasculatures", Arthrioscler Thromb Vasc Biol, vol. 32, Dec. 31, 2012, p. 5.
Office Action dated Jan. 30, 2019 relating to Israeli Patent Application No. 256673.

\* cited by examiner

*Primary Examiner* — Ruth A Davis
(74) *Attorney, Agent, or Firm* — Dinsmore & Shohl LLP

(57) ABSTRACT

A bona fide adaptable in vitro microcirculation model is provided by integrating a 3-D printed network of endothelial-cell lined perfusion channels, formed via sacrificial casting in a gel matrix, with a native, adaptable microvasculature matured from native microvessels added to the gel matrix. Responsive vascular adaptation exhibited by the in vitro microcirculation is physiologically relevant. Methods for fabricating, devices, models and investigative platforms for pharmaceutical applications, vascular mechanism and microvessel-parenchyma interaction studies, and vascularizing strategies for tissue engineering applications are also disclosed.

20 Claims, 14 Drawing Sheets

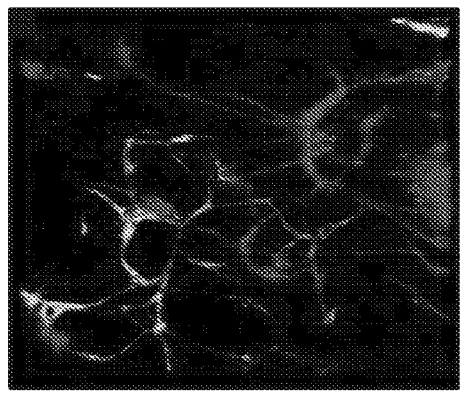 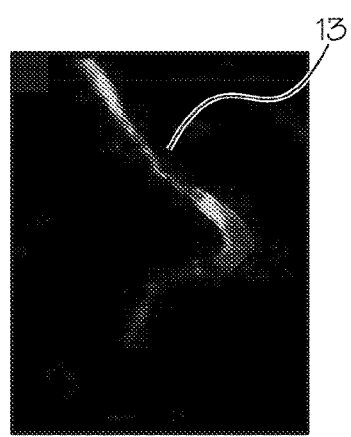
FIG. 14A  FIG. 14B
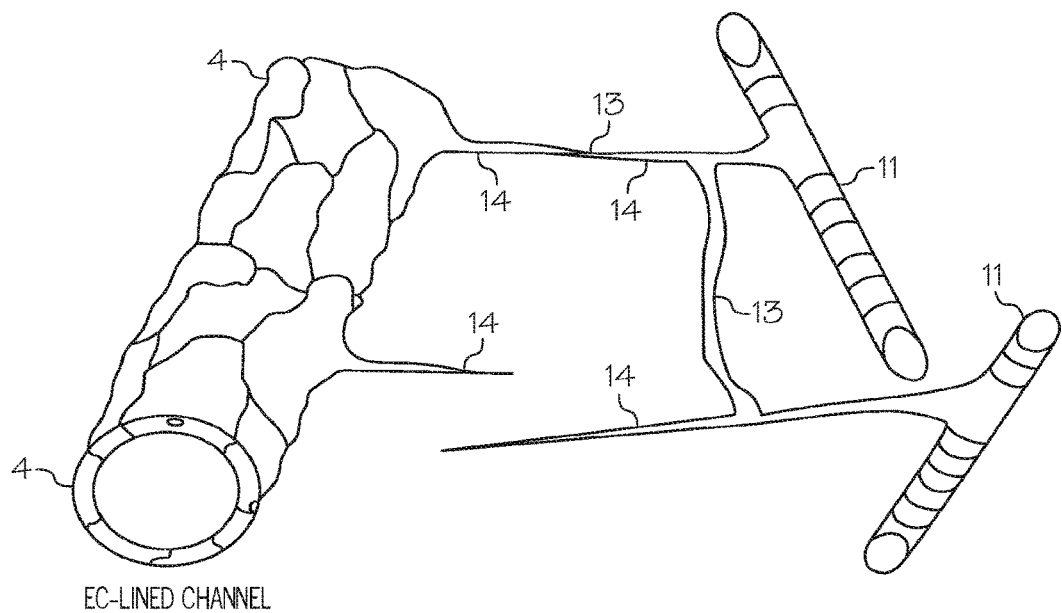
FIG. 14C

VASCULARIZED IN VITRO PERFUSION DEVICES, METHODS OF FABRICATING, AND APPLICATIONS THEREOF

PRIORITY

This application claims benefit under 35 U.S.C. § 119(e) to U.S. provisional application No. 62/188,803, filed Jul. 6, 2015, and U.S. provisional application No. 62/279,019 filed Jan. 15, 2016, the entire disclosures of which are incorporated herein by this reference.

TECHNICAL FIELD

The technical field relates broadly to high throughput biomedical investigation utilizing a positively adaptable in vitro perfusable microcirculation device with specific applications in the fields of pharmaceutical screening/testing, tissue and organ fabrication and transplant, toxicity screening, and for investigating response of vasculature to a variety of stimuli and conditions.

BACKGROUND

Effective tissue fabrication depends on the incorporation of an integrated vascular system into the tissue construct. The vasculature itself is a complex, multi-cellular system with unique but different biological requirements. At the single vessel level, the general structure entails a tube of which the walls are comprised of different cellular layers, each of which impart structural and functional characteristics to the vessel. However, a single vessel will contribute effectively to tissue perfusion only when incorporated into a vascular network. Any one vascular network entails in-flow and outflow vessels (arteries and veins) delivering and draining blood to and from the downstream distribution and tissue-interface vessels (the microvasculature).

The ability to establish and maintain a functional, adaptable microcirculation in vitro has the potential to significantly impact a broad array of biomedical arenas. In virtually every discussion concerning the building of tissue replacements, the critical importance of having a microvasculature integrated into the tissue construct is stressed. In cellular assay platforms, the presence of a perfused vasculature in combination with the target parenchyma cell is considered to improve the utility of the assay beyond having just parenchyma cells. An in vitro perfused microvasculature model with a functional, truly adaptive microcirculation would permit investigation of the mechanisms of microvascular form and function, such as how flow affects angiogenesis, and those mechanisms underlying microvessel wall and network remodeling. Drug discovery, investigation of vascular disease mechanics, and environmental chemical toxicity, are all areas with the potential to be benefited by development of an in vitro, perfusable microvasculature that fully recapitulates physiological microcirculation function and adaptability.

Formally, a microcirculation is a system of blood circulation through the microvasculature. Importantly, a microvasculature capable of supporting effective circulation consists of a properly arranged hierarchical tree of heterogeneous vessel types producing a network topology forming inflow (arterioles), exchange (capillaries), and outflow (venules) pathways. The individual microvessels that make up a network are complex structures made up of not only endothelial cells but also a variety of mural cells, all of which are necessary to form a stable and adaptable microvessel. The ability of the entire network to adapt and appropriately remodel in response to a variety of hemodynamic cues is a necessary homeostatic activity intrinsic to all microvasculatures, and is thought to reflect, in part, an effort by the vessels to normalize hemodynamic forces (herein called "resistance-based adaptation". This ability is an important determinant of endothelial cell health and function. Thus, an ideal in vitro microcirculation is a perfused microvasculature that is comprised of all of the vascular cells required for recapitulating these core microvascular activities.

A key goal of current innovation is therefore generation of a truly adaptable functional in vitro microcirculation. A network of human vessels is required to create and maintain 3-D tissues of physiologically relevant proportions. One early strategy for creating vascular-like perfusion circuits involved lining pre-formed channels of microvessel-like dimensions (usually 6-200 μm in diameter) with vascular cells. A common approach to forming these "microchannels" utilized standard soft lithography to mold vascular-compatible matrices into 2-D or 3-D channels which are subsequently lined with endothelial cells (and sometimes mural cells). This general strategy has been successfully used to form predominately parallel, endothelialized channels as part of a microfluidic-based "vascularized" system. In many respects, however, the "vessels" formed are merely lined walls of channels with fixed microvascular dimensions in a fixed network topology. (See, e.g. U.S. Pat. No. 8,663, 625 to Stroock et al.) Consequently, while useful in applications benefiting from an endothelial cell-lined perfusion circuit (e.g. such as in biochip applications), such vascularized systems are limited in their ability adapt to hemodynamic changes and parenchyma requirements.

Recently, a team of investigators purported to have developed a "living and dynamic" in vitro perfused human capillary network that is metabolically responsive and adaptable. (U.S. Ser. No. 13/253,820, titled "High-Throughput Platform Comprising Microtissues Perfused With Living Microvessels" to George et al. published Apr. 5, 2012, and *Tissue Engineering*: Part C Vol. 19, 2013 p 1-8, collectively referred to herein as "George".) According to George, the system provides matrix, cells and angiogenic stimuli that allow "capillaries' to self assemble into a continuous network and subsequently anastomose with adjacent fluidic channels to form a "living dynamic" in vitro microcirculation perfusable at physiological flow and shear rates. The in vitro microcirculation of George, however, is not a native, bona fide microcirculation. The George lab utilized cultured, single cells that assembled into cellular tubes that connected the microfluidic channels to each other through the seeded microtissue. George refers to the cellular tubes as "vessels," and has demonstrated that the tubes re-orient and inosculate. To this extent they are not unlike capillaries, however do not have the complex, multicellular, multi-laminate structure of native arterioles or venules and do not, therefore, exhibit appropriate resistance-based adaptation nor true microvessel function.

"Microcirculation" is generally taken morphologically, to encompass all of the blood vessels with a diameter of less than 150 μm, that is, some small arteries, arterioles, capillaries, and venules. The complexity and hemodynamic response of each type of vessel is unique. Capillaries are generally the most simple vessels, ranging from 4 to 12 μm in diameter of which the walls are composed exclusively of endothelial cells, each endothelial cell, rolled up in the form of a tube and composing one segment of the capillary. Arterioles and venules, on the other hand, are multilaminate, complex, and arterioles in particular include a thicker myogenic layer that is largely responsible for resistance-based adaptive remodeling. Each type of vessel responds differently to flow hemodynamics and a native microcirculation includes a network of microvessels composed necessarily of all three types. An in vitro microcirculation must at least recapitulate these functionalities in order to be truly adaptive. At the very most, the protocol of George results in a network of immature capillaries.

Established microcirculation tenets say that an immature, dysfunctional microvessel network will eventually resolve down to a single, large caliber microvessel since the elements necessary to establish proper network architecture/topology are not in place. Persons of skill in the microcirculation arts commonly refer to this as a "shunt problem" (described and exemplified in Pries, et al. The shunt problem: control of functional shunting in normal and tumor vasculature. *Nature Reviews* Vol. 10, August 2010, pp 587-593).

Interestingly, this reductive disappearance of microvasculature in favor of a single larger tube was exhibited by the George "microcirculation" in response to physiological flow parameters and was presented as evidence that the in vitro "microcirculation" was capable of adaptation. A normal part of microcirculatory adaptation is indeed the capacity to delete extraneous neovessels from a network. Too much of this "pruning," however, leads to microvessel rarefaction (disappearance of the capillary bed) and reflects a dysfunctional microcirculation. The neovasculature of George did not include vessels having a native mural layer, which is the myogenic layer responsible for adapting the vessel morphology/diameter in response to changing hemodynamic forces. In the absence of this capacity, the vessel is damaged and pruning is triggered. Microcirculation adaptability and remodeling is a dynamic process dependent on a complex and not completely understood interplay of various growth factors, hemodynamic forces, and vessel health status. Adaptive, positive, outward remodeling is a reactive and compensatory response to stimuli and stress. Maladaptive negative-inward constrictive remodeling eventually results in narrowing and disappearance of microvessels, and the resulting microcirculation rarefaction. Although George is technically correct in characterizing the observed rarefaction as an adaptation, a person skilled in the art of microcirculation recognizes that this adaptation is inappropriate and reflects a dysfunctional, unstable in vitro "microcirculation" of limited investigative utility.

Recapitulating a truly functional physiological neovascularization requires more than the generation of new vessel elements. Physiological neovascularization requires vascular guidance and inosculation, vessel maturation, pruning, A-V specification, network patterning, structural adaptation, intussusception, and microvascular stabilization. Without the concomitant capacity for neovessel remodeling and adaptation, networks of simple, non-specialized vessel segments give rise to a dysfunctional microcirculation.

In the case of in vivo engineering of microcirculations for implantation, nearly two decades of research has established that incorporation of endothelial cells alone (particularly human endothelial cells) into a tissue scaffold does not effectively result in formation of a stable microvasculature once implanted. The presence of additional perivascular cells or precursors, such as smooth muscle cells, mesenchymal smooth muscle precursors (e.g. 10T1/2 cells), and/or tissue stromal cells in the engineered system promotes neovascularization and is needed for long-term microvascular stability. It was previously established that new stable microvessel segments may be integrated into a microfluidic network via angiogenesis (formation of new vessels from existing vessels) and neovascularization (formation of a circulatory network). This is perhaps best highlighted in the use of isolated, intact microvessel segments, which retain the native microvessel structure (Hoying et al. Angiogenic potential of microvessel fragments established in three-dimensional collagen gels. *In Vitro Cell Dev Biol Anim.* 1996; 32:409-419, the entire disclosure of which is incorporated herein by this reference), to rapidly form a mature, functional microcirculation in vivo. Hoying and his colleagues later developed and characterized an experimental model of tissue vascularization based on the implantation of this microvascular construct, which was shown to rapidly inosculate with recipient host circulation and to recapitulate physiological angiogenesis, vessel differentiation, and network maturation (Hoying et al. Rapid Perfusion and Network Remodeling in a Microvascular Construct after Implantation, *Arterioscler Thromb Vasc Biol.* 2004 May; 24(5):898-904, the entire disclosure of which is incorporated herein by this reference). While the perivascular cells in these composite vascular tissue constructs play multiple roles related to neovascularization, an important function of these cells is to maintain neovessel stability.

Creating a microenvironment that enables growth of an in vitro microtissue perfused with living microvessels (e.g., arterioles, capillaries, and venules) represents a completely new paradigm. By definition, a 3-D tissue requires enhanced transport of nutrients and waste relative to 2-D monolayer cultures. Current approaches to create such an environment include: 1) enhanced concentration gradients of nutrients and waste while relying on molecular diffusion as the mode of transport, 2) creation of microchannels in the tissue to enhance advection (forced convection), and 3) forced interstitial fluid flow. In vivo, diffusion of nutrients and waste is the mechanism of transport once solutes exit the capillary bed, and is generally limited to distances <250 µm. The rate of transport is proportional to the concentration difference between two points, and inversely related to the separation distance. Hence, numerous 3-D tissue models have been reported with dimensions on the order of 1-10 mm by simply enhancing the oxygen tension (room air is 160 mmHg compared to 20-30 mmHg in the interstitial tissue) and concentration of other nutrients (e.g., glucose). Clearly, development of a truly functional, adaptive microcirculation is an important step in the evolution of 3-D tissue and organ fabrication technology.

Thus, although the ability to generate living adaptable microvessels in 3-D networks that become functional upon implantation has been demonstrated, development of a stable and adaptable in vitro microcirculation has not heretofore been achieved.

There remains a need for an in vitro perfusion device vascularized with a recapitulated physiological microcirculation that is stable and appropriately adaptable and which may be subjected to stimuli/putative agents/forces via perfusion or environmental/nutritional manipulation for a variety of downstream applications and for continued investigative utility.

SUMMARY

Accordingly, the present investigators provide a functional, stable and appropriately adaptable in vitro perfusable microcirculation by integrating a printed network of perfusion channels, via sacrificial casting and subsequent lining with endothelial cells, with a native, intact microvasculature.

Under perfusion conditions, endothelial sprouts from the channels and the native microvessels inosculate to form a stable microcirculation. The resultant in vitro microcirculation is positively adaptable and can support subsequent studies examining mechanisms of microvascular form and function, microvessel-parenchyma interactions, pharmaceutical effects, and vascularizing strategies for tissue engineering. "Native" as utilized herein means isolated from an organism.

One embodiment is directed to a vascularized in vitro perfusion device comprising an adaptable microcirculation that is stable at physiologically relevant perfusion conditions. "Adaptable" means capable of undergoing vessel-appropriate adaptive remodeling in response to a hemodynamic or environmental stimuli or condition. "Stable" means that the microcirculation maintains the ability to appropriately adapt and does not undergo spontaneous or inappropriate reduction in the microvascular density. "Physiologically relevant conditions" are those that mimic living biological conditions.

Another embodiment provides a vascularized in vitro perfusion device 1 comprising an adaptable microcirculation, said device comprising: a supporting structure 2 comprising a gel matrix 3, a fabricated network of microfluidic endothelial cell-lined channels 4, said network comprising an inlet channel 5, an outlet channel 6, and at least one cross channel 7 connecting the inlet channel 5 to the outlet channel 6, said cross channel 7 positioned at least partially within the gel matrix 3, an inlet port 8 in fluid communication with the network 4, and an outlet port 9 in fluid communication with the network 4, and a neovasculature 10, said neovasculature being derived from intact native microvessels 11 incorporated into the gel matrix 3 and subject to maturing conditions, wherein the network 4 is in vascular communication with the neovasculature 10 to form an adaptable microcirculation. In certain aspects the device further comprises living cells 16 populating the gel matrix 3 and derived from one or more tissue types. In some embodiments, one or more device embodiments may be organized into a system 17 wherein the devices are assembled to be perfusable in series or in parallel or in some combination thereof.

Another embodiment is directed to a method of manufacturing a stable and adaptable in vitro microcirculation system, the method comprising: a) casting a network of channels on a polymerized matrix gel with a sacrificial material, said network cast to form at least one perfusion inlet port and inlet channel, and at least one perfusion outlet port and outlet channel, and one or more cross channels, each cross channel being in communication with both an inlet channel and an outlet channel; b) incorporating an isolate of intact native microvessels into a polymerizable matrix; c) distributing the polymerizable matrix from step b) over the network of cast channels and polymerizing the matrix to form a continuous polymerized gel matrix comprising both the network of cast channels and the intact native microvessels; d) incubating the gel matrix under conditions suitable to promote spontaneous growth of a neovasculature from the native microvessel isolate, said incubating optionally taking place before or after step c); e) flushing the sacrificial material from the cast network to yield a molded network of channels; f) lining the molded channels with endothelial cells to form a continuous network of endothelial cell-lined channels; and g) subjecting the network of endothelial cell-lined channels to perfusion with a perfusion fluid sufficient to induce endothelial sprouting from the one or more cross channels and inosculation between at least two sprouts and the neovasculature, thereby forming a stable adaptable microcirculation system.

Other embodiments are directed to pharmaceutical agent screening devices comprising the vascularized in vitro perfusion device according to embodiments of the invention, wherein the living cells comprise target parenchymal cells. Methods for screening putative pharmaceutical agents for target pharmaceutical efficacy using the embodiments of the inventive device comprise: formulating (1) a control perfusion fluid and (2) a test perfusion fluid comprising at least one putative agent; perfusing the adaptable microcirculation with (1); perfusing the adaptable microcirculation with (2); and comparing the results to determine pharmaceutical efficacy.

These and other embodiments will be clarified and more readily understood by reference to the Figures and Detailed Description, below. Nonetheless, the Figures and Detailed Description disclose specific embodiments for illustrative purposes and should not be construed as limiting the full scope of the invention as defined by the appended claims.

Figure 1:
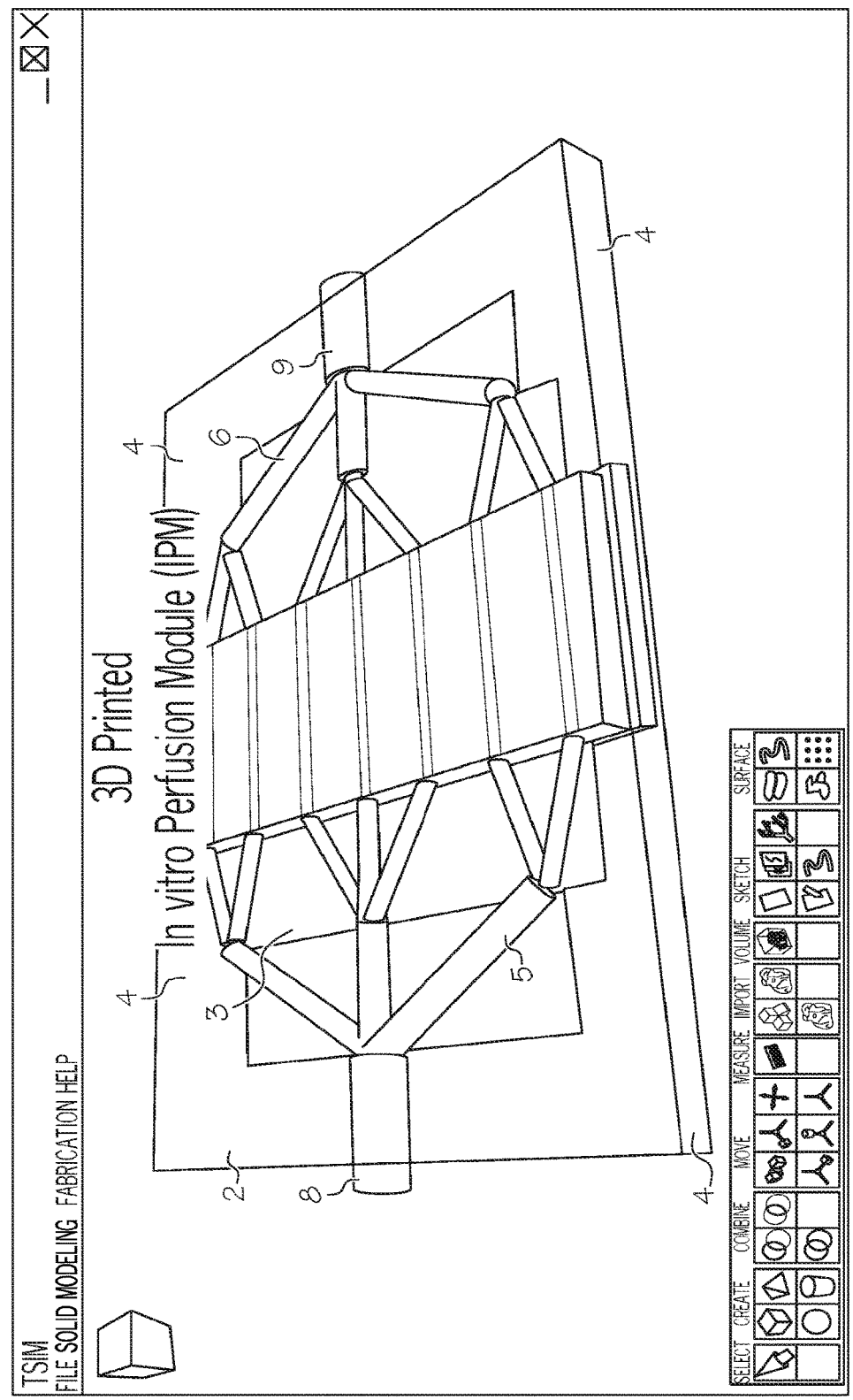
FIG. 1. User interface showing tissue structure information modeling (TSIM) software-generated In vitro Perfusion Module (IPM) Static Model set up for 3-D printing on BioAssemblyBot™ platform.

from the microvessels (dark arrows); 13(C) a contiguous neovasculature is formed after 7 days; 13(D) after implantation a stereotypical microcirculation forms (highlighted by ink casting via the host circulation).

FIG. 14(A) micrograph showing spontaneous inosculation between EC-lined channel derived sprouts (green) and microvessel-derived sprouts (red) 14(B) a magnification of an inosculation event in (A) 14(C) Schematic of an inosculation connecting the channel network and the neovasculature.

DETAILED DESCRIPTION

Recapitulation of a bona fide, native microcirculation in vitro would enable a broad spectrum of research (microvascular biology), clinical (regenerative medicine) and commercial (vascularized tissue mimics) activities. In contrast to cell-lined channels which have limited remodeling capabilities, a true microcirculation adapts to match perfusion needs with the surrounding parenchyma and by integrating with the tissue function. Generally, the present disclosure provides a vascularized in vitro perfusion device having a network of endothelial cell-lined channels vascularly connected to a "downstream" native, self-forming neovasculature in a microfluidic platform. The native neovasculature is derived via angiogenesis from isolated, intact microvessels and is formed within polymerizable biological gels. The neovasculature spontaneously matures into a bona fide microcirculation in response to perfusion derived hemodynamic cues. The cell-lined channel network is connected to an external microfluidic control system to provide the necessary perfusion to the native neovasculature and therefore drive and control its maturation into a functional and adaptive in vitro microcirculation.

Thus, embodiments of the invention are directed to a vascularized in vitro perfusion device comprising an adaptable microcirculation that is stable at physiologically relevant perfusion conditions, methods of manufacturing the devices, as well as downstream applications.

By convention, an in vitro perfusion module that has not been populated with native microvessels and/or does not comprise a neovascular microcirculation may be referred to herein as an "IPM," whereas an in vitro perfusion module comprising native microvessels and/or a neovascular microcirculation may be referred to herein as a "VIPM."

Macrovessels and microvessels display significant differences in vessel wall structure. These structural differences also reflect wall compositional differences. While all vessels are lined by a single monolayer of endothelial cells (ECs), the numbers and types of cells comprising the additional layers of the vessel wall vary considerably. For example, conduit arteries contain multiple circumferential layers of smooth muscle and stroma cells, elastin sheets, and extracellular matrix. Microvessels contain considerably fewer cells and less matrix mass, and many of the mural cell types are specialized. Furthermore, the mural cell layers represent a continuum in phenotype from the more muscular, circumferentially oriented smooth muscle cells in arterioles to the sparsely covered, muscle-like pericytes in the capillaries. The present investigators exploit this native complexity by utilizing intact, native microvessels to seed formation of the neovasculature.

The cellular building blocks commonly used in fabricating vasculatures include a variety of endothelial cells or endothelial cell precursors (although HUVECs are frequently used) and mural/perivascular cells such as smooth muscle cells, pericytes, and mesenchymal smooth muscle precursors. With respect to the endothelial cell (EC), it does not appear that the origin of the EC is critical; conduit ECs are capable of assembling into microvessels and microvessel ECs are able to establish a luminal lining in conduit vessels. Endothelial cells (or endothelial precursor cells) are necessary and sufficient for establishing the initial vessel and network structure. While not essential in the initial vessel formation, inclusion of mural cells facilitates vascular assembly, in part, by stabilizing the immature vasculature. Many of the fabrication strategies, particularly for microvasculatures, rely on the intrinsic ability of these vascular cells to self-assemble into vessels, which occurs more readily in a 3-D environment. This self-assembly ability likely reflects a more generalized behavior whereby cells actively aggregate with like-cells via homotypic adhesion molecules specific to endothelial cells. It also reduces considerably the challenges in vascular fabrication. Since it's not necessary to place individual cells into specific positions within the vessel wall, the task is reduced to simply patterning the cells with the expectation that vessel assembly and network formation will happen spontaneously within the pre-determined pattern.

Sacrificial 3-D printing represents a relatively new approach to form endothelialized microfluidic channels for tissue construct perfusion. The technique involves the use of sacrificial materials to form channels. Once printed in the correct topology and surrounded by matrix, these materials are then flushed out of the system leaving behind open conduits which are subsequently sodded with vascular cells. BioAssemblyBot® 3-D printing and robotics systems (available from Advanced Solutions Life Sciences, LLC of Louisville, Ky.) are used to fabricate endothelial cell-lined channels using a sacrificial casting approach as a means to connect the native microvessel-derived neovasculature to an external perfusion source. The in vitro perfusion module (IPM), with its sacrificial channels, can then serve as an enabling platform for a spectrum of perfusable, complex cell-based assays by flushing the channels and adding cells of interest to both the walls of the channels (now open following removal of the sacrificial material) and/or the surrounding matrix.

Recently, channels were pre-formed in a 3-D matrix by directly dispensing carbohydrate solutions that harden into a glass to form a cast of the desired microvascular network (see Miller J S et al. "Rapid casting of patterned vascular networks for perfusable engineered three-dimensional tissues" *Nature materials.* 2012 September; 11(9):768-74, the entire disclosure of which is incorporated herein by this reference). The glass was then dissolved and seeded with vascular cells forming a perfusable, vascular cell-lined, channel network.

Once cast in the correct topology and surrounded by matrix, these materials are then flushed out of the system leaving behind open conduits which are subsequently sodded with vascular cells. This same sacrificial approach was used to form implantable microvascular networks using patterned Pluronic hydrogel placed in a collagen matrix as the channel-forming material, see Hooper R C et al. "Fabrication and In Vivo Microanastomosis of Vascularized Tissue-Engineered Constructs" *Tissue Eng Part A.* 2014 May 19, the entire disclosure of which is incorporated herein by this reference. In this most recent approach, the pre-built microvasculature was incorporated into a host circulation via anastomotic attachments to a feed artery and vein, thereby providing immediate perfusion of the fabricated vascular system.

For convenient reference to the Figures, the following numerical designators apply:
1 in vitro perfusion device
2 support structure
3 gel matrix
4 network of endothelial cell-lined channels
5 inlet channel
6 outlet channel
7 cross channel
8 inlet port
9 outlet port
10 neovasculature
11 microvessels
12 enclosure
13 inosculation
14 sprout
15 control system
16 living cells
17 sections
18 tissue According to some embodiments, a vascularized in vitro perfusion device 1 comprising an adaptable microcirculation is provided. The device may comprise: a supporting structure 2 comprising a gel matrix 3, a fabricated network of microfluidic endothelial cell-lined channels 4, said network comprising an inlet channel 5, an outlet channel 6, and at least one cross channel 7 connecting the inlet channel 5 to the outlet channel 6, said cross channel 7 positioned at least partially within the gel matrix 3, an inlet port 8 in fluid communication with the network 4, and an outlet port 9 in fluid communication with the network 4, and a neovasculature 10, said neovasculature being derived from intact native microvessels 11 incorporated into the gel matrix 3 and subject to maturing conditions, wherein the network 4 is in vascular communication with the neovasculature 10 to form an adaptable microcirculation. In some embodiments, the device 1 further comprises an enclosure 12, although it is contemplated that the device 1 may be constructed to be of a more temporary nature, or may be mounted without an enclosure for investigational or observational purposes. The enclosure 12 may be fabricated from any suitable material, for example a plastic. In some embodiments the enclosure 12 comprises a rigid transparent outer shell. It may be desirable to provide the device as a sealed system and the enclosure may be fabricated directly by bioprinting in a single workflow with the device as either an open or sealed system. In certain aspects the enclosure may include a lid. In very specific embodiments, the enclosure comprises a biocompatible plastic housing, and in more specific embodiments the plastic comprises a transparent plastic. In even more specific embodiments the plastic is selected from an acrylic, styrene and carbonate polymer plastic, and in very specific embodiments the plastic comprises a transparent polyacrylate. Non-limiting examples of specific suitable brands of polyacrylates include Plexiglass, Lucite, Perspex, Oroglass, Optix, and Altuglass polyacrylate plastic.

In particular embodiments, the device is constructed with at least one inlet port 8 and at least one outlet port 9, all ports being accessed exterior to the enclosure 12. An external perfusion control system 15 may be in operational communication with the network 4 through the inlet and/or outlet port 8/9. In specific embodiments operational communication is through the inlet port 8.

According to specific embodiments, the gel matrix 3 comprises any suitable polymerizable gel that sustains biological growth. In more specific embodiments the gel is selected from a biological gel. Non-limiting examples include a collagen gel, a fibrin gel, and combinations thereof. In very specific embodiments the gel matrix is a collagen gel matrix. In some specific embodiments, the intact native microvessels are derived from one or more of adipose, brain, islet, and omentum. In very specific embodiments the intact native microvessels 11 are derived from adipose tissue, and in even more specific embodiments, the intact native microvessels are derived from human adipose tissue.

Perfusion from the endothelial cell-lined channels 4 into the neovasculature 10 occurs via inosculation 13 between endothelial cell sprouts 14 from both the channels 4 and neovessels 10, thereby establishing lumen continuity between the channels 4 and the neovasculature 10. Subsequent maturation of this immature neovasculature is driven by controlled pressure or flow across the system. It is this native microvessel-derived microvasculature supplied by the channel network that serves as the functional microcirculation. The requisite vascular communication and lumen continuity, therefore is formed from perfusion-driven sprouting from the network of endothelial cell-lined channels 4, and inosculation 13 between at least two sprouts 14 and the neovasculature 10. A neovasculature is "adaptable" in accordance with the present disclosure if it exhibits an ability to undergo vascular differentiation and/or positive vascular remodeling in response to at least one perfusion-driven hemodynamic force or stimuli. Intravascular pressure and shear stress may be modulated to drive, for example, differentiation of immature neovasculature into venules or arterioles, with the latter generally constituting resistance vessels of a smaller diameter, thus maturing the neovasculature into a bona fide adaptable microcirculation. Accordingly, an adaptive microcirculation aspect of the invention matures from an adaptive neovasculature.

According to some embodiments, the gel matrix 3 may be populated with living cells 16 derived from one or more tissue types. In one aspect, living cells may be printed in an IPM or VIPM and studied under a variety of controlled experiments. A microscope slide may be assembled into the cell structure to enable real time view of IPM dynamics. The gel matrix 3 may be populated with cells from one tissue type 18, or multiple tissue types, or the matrix may be divided into at least two sections 17 with each section aligned with at least one cross channel 7 of the network 4, and populated with a cell from a distinct tissue type. In very specific embodiments the living cells are human. According to investigative or drug design needs, non-limiting examples of suitable living cells include normal cells, diseased cells, stem cells, endothelial cells, stromal cells, epithelial cells, neuronal cells, connective cells, myocardial cells, hepatocytes, renal cells, tumor cells, liver cells, pancreatic cells, muscle cells, brain cells, kidney cells, and patient-specific cells. It is understood that these categories of cells are not mutually exclusive and may substantially overlap or subsume one another. Where the gel matrix 3 is populated by living cells 16, the cells may provide cues that promote vascular remodeling in the in vitro microcirculation.

In one specific embodiment, a perfusion fluid comprises a putative pharmaceutical agent that has a target effect on a cell derived from a particular tissue. A metric of the effect may comprise a measurement of an adaptive or maladaptive response by the in vitro microcirculation to presence of the agent. In another specific embodiment, perfusion parameters may defined to replicate a physiopathology such as hypertension, and a perfusion fluid may comprise an putative pharmaceutical agent. In accordance with some embodiments, living cells may be provided in the form of microtissue constructs.

According to some embodiments, the IPM or VIPM is configured as a pharmaceutical agent screening device populated with living cells comprising target parenchymal cells. In specific embodiments, the target parenchymal cells comprise one or more of kidney cells, liver cells, and cardiac cells. In very specific embodiments the target parenchymal cells comprise cardiac cells and the putative agents are screened for efficacy in modulating cardiac remodeling.

Methods for screening putative pharmaceutical agents for target pharmaceutical efficacy are also contemplated. According to some method embodiments, (1) a control perfusion fluid is formulated and (2) a test perfusion fluid comprising at least one putative agent is formulated; an in vitro adaptable microcirculation is perfused the control perfusion fluid and either the same or a different in vitro adaptable microcirculation is perfused with the test perfusion fluid. The results are compared to determine pharmaceutical efficacy. A "control" perfusion fluid may not comprise the agent, or may comprise an agent of known pharmaceutical efficacy.

Figure 9:
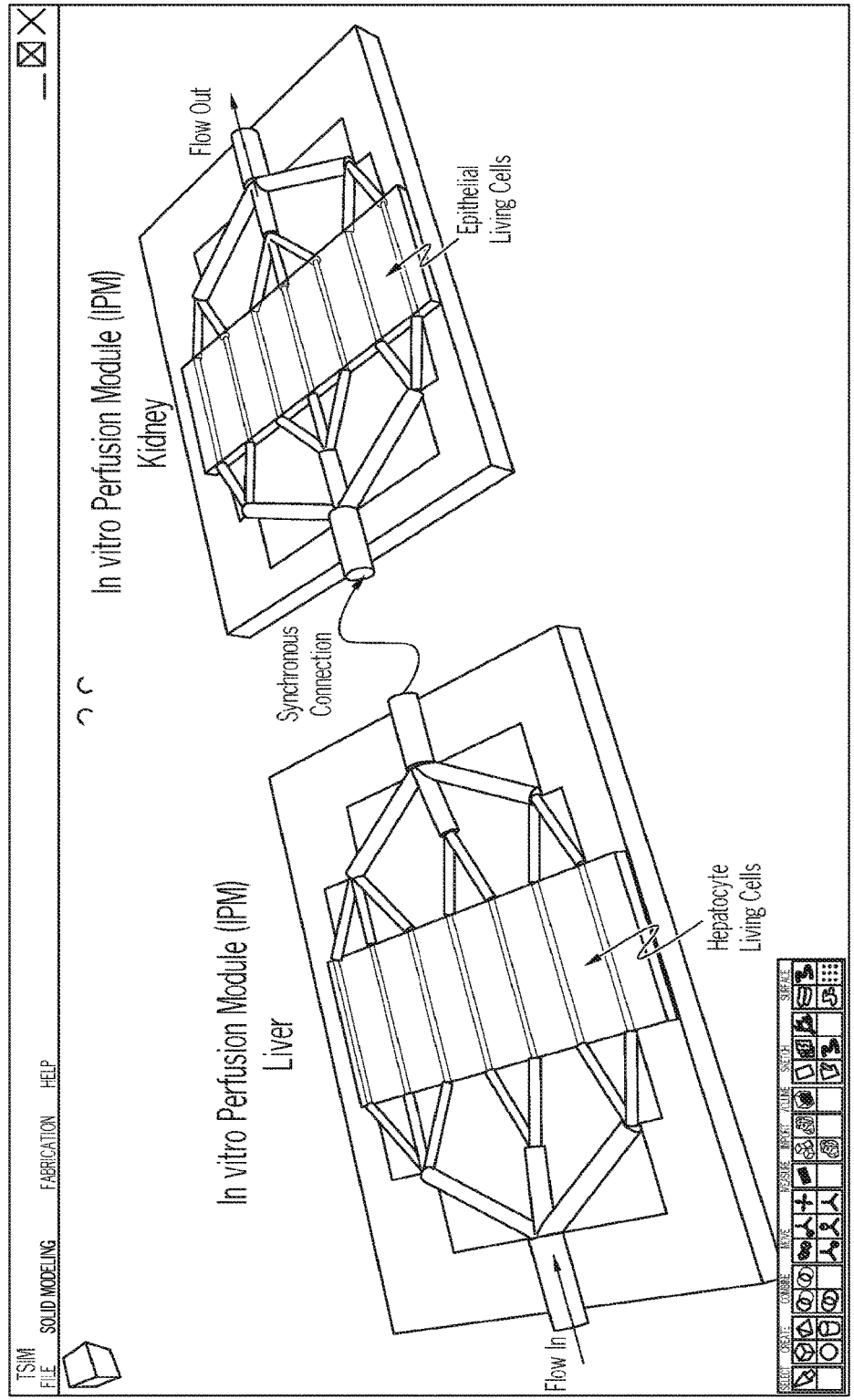
FIG. 9. Illustration of a liver (populated with living hepatocyte cells) IPM in series with a kidney (populated with living epithelial cells) IPM.
Figure 10:
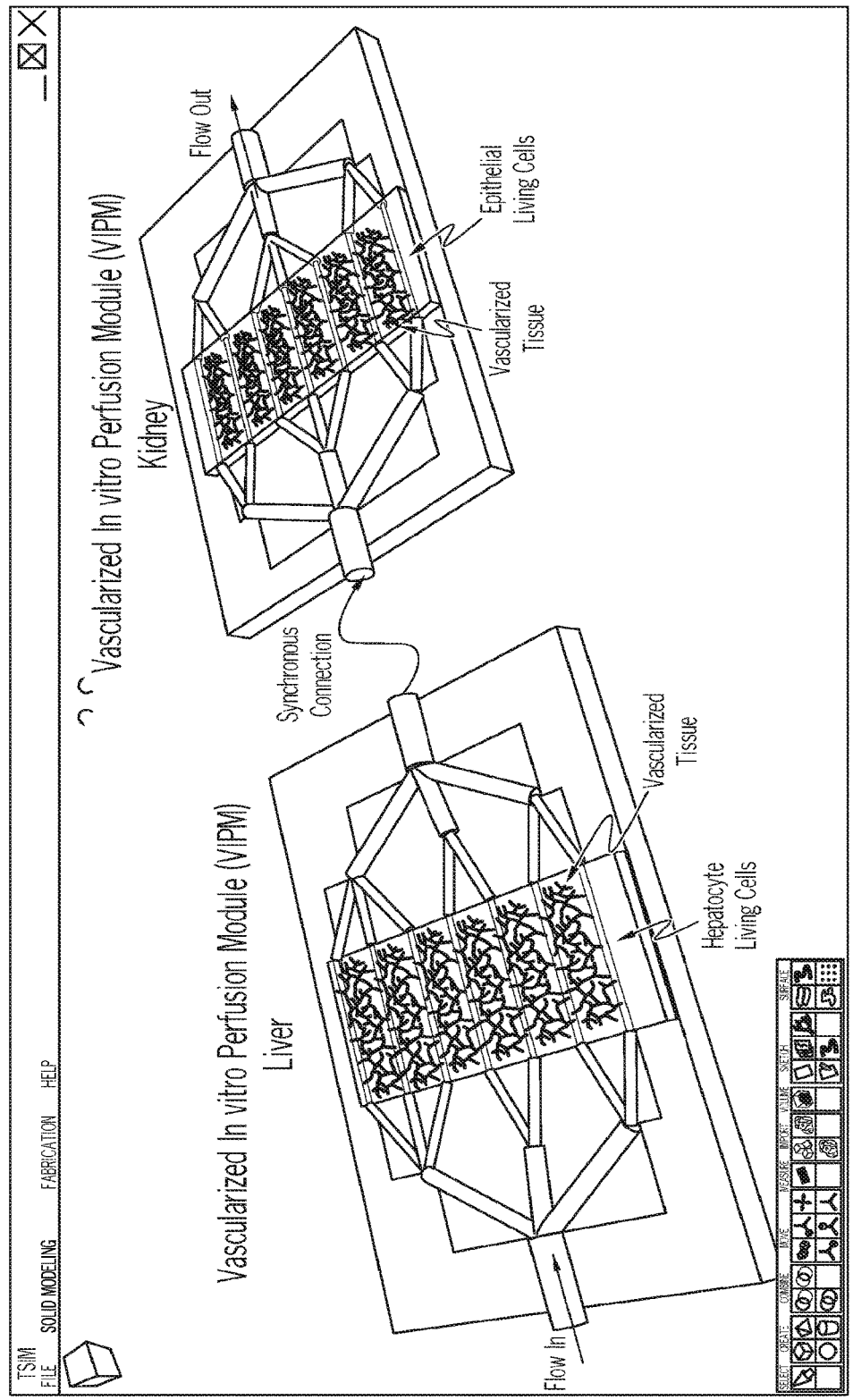
FIG. 10. Illustration of a liver (populated with living hepatocyte cells) VIPM in series with a kidney (populated with living epithelial cells).
Figure 11B:
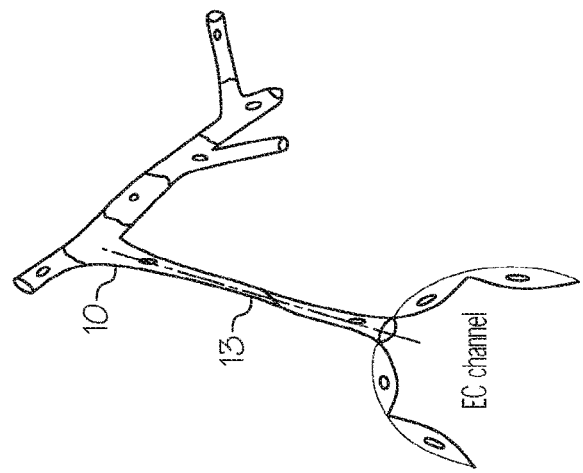
FIG. 11(A). Schematic of another embodiment (ladder style) of an enclosed vascularized in vitro perfusion module; 11(B) magnified graphic of inosculation between a sprout from an EC-lined channel and a sprout from a neovasuclature to form lumen continuity.
Figure 11A:
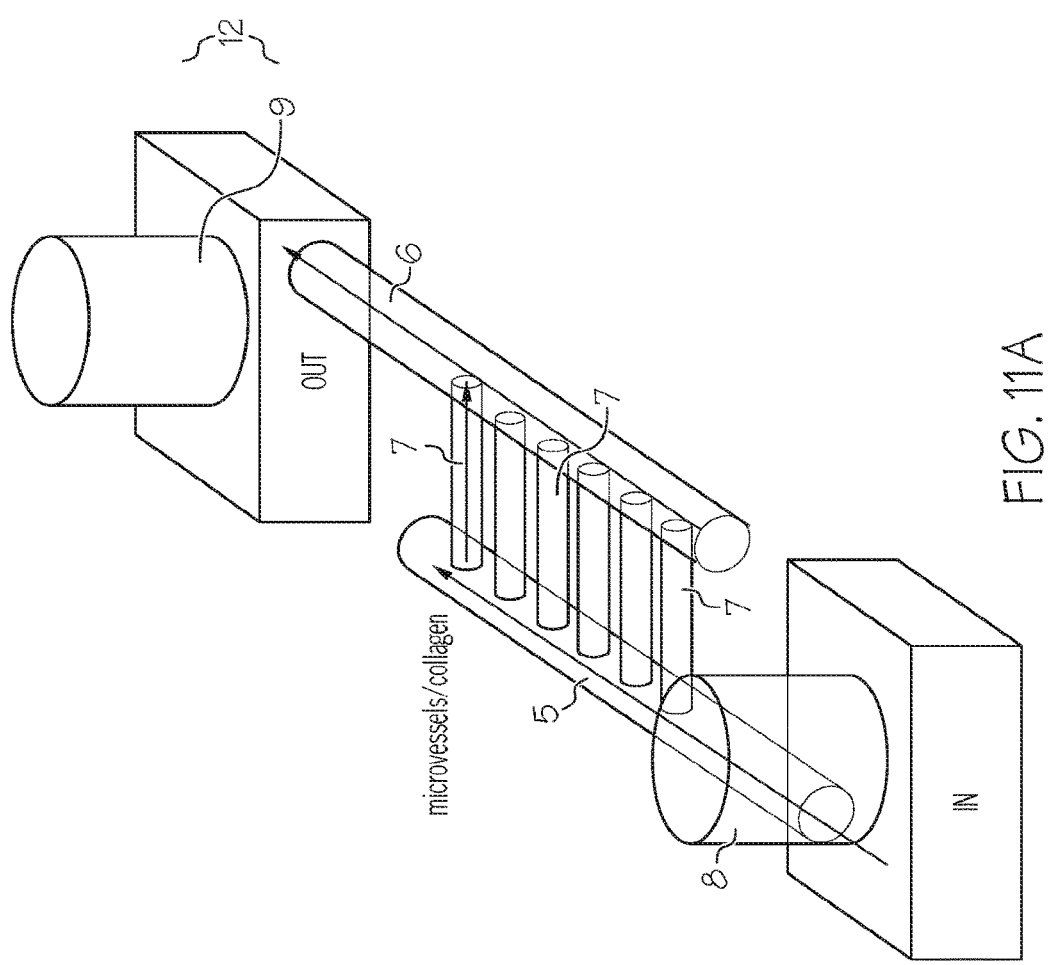
Figure 12A:
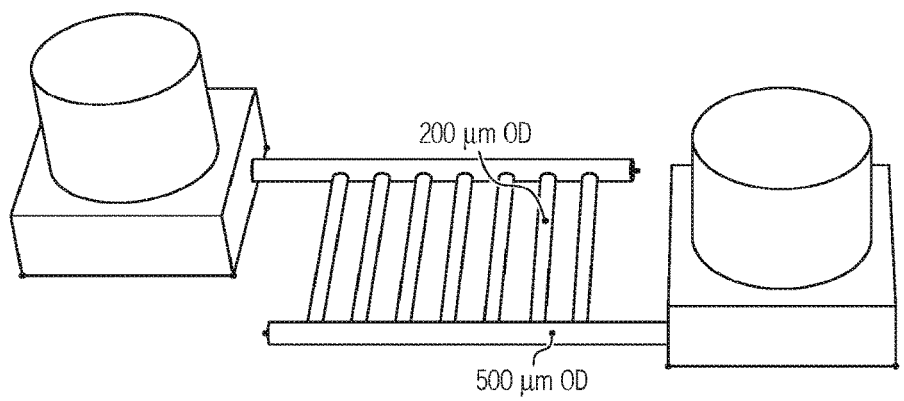
FIG. 12(A). Illustration of a digital prototype of an exemplary channel system to be printed; 12(B) the 3-D printed prototype using a pluronic gel; 12(C) illustration of CAD simulations of a particular model generated using TSIM software showing a shear stress of 10 dynes/cm$^2$.
Figure 12B:
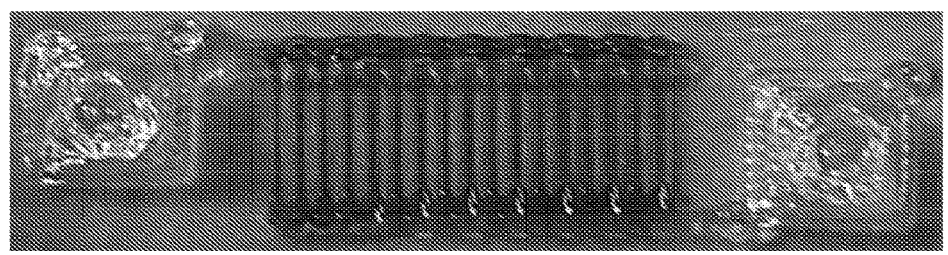
Figure 12C:
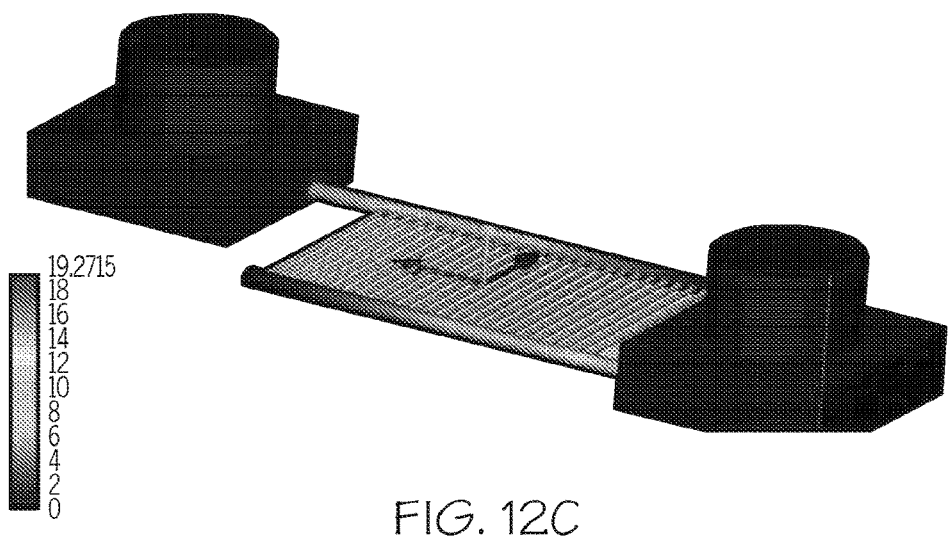
Figure 13A:
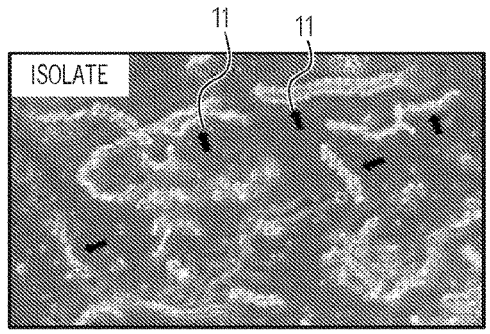
FIG. 13(A). Isolated microvessels cultured in 3-D collagen (dark arrows); 13(B) sprouting neovessels (open arrows)
Figure 13B:
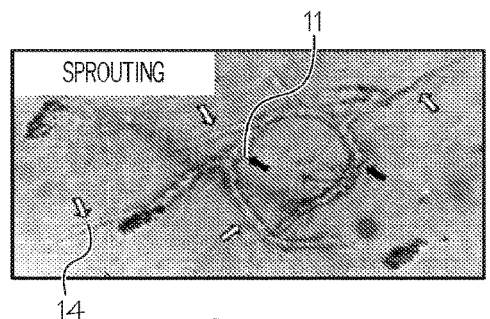
Figure 13C:
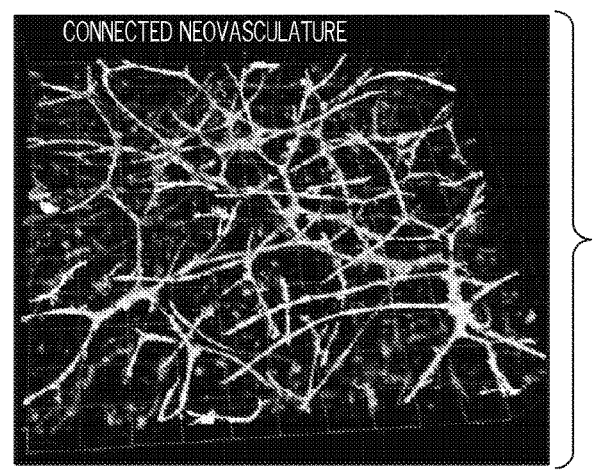
Figure 13D:
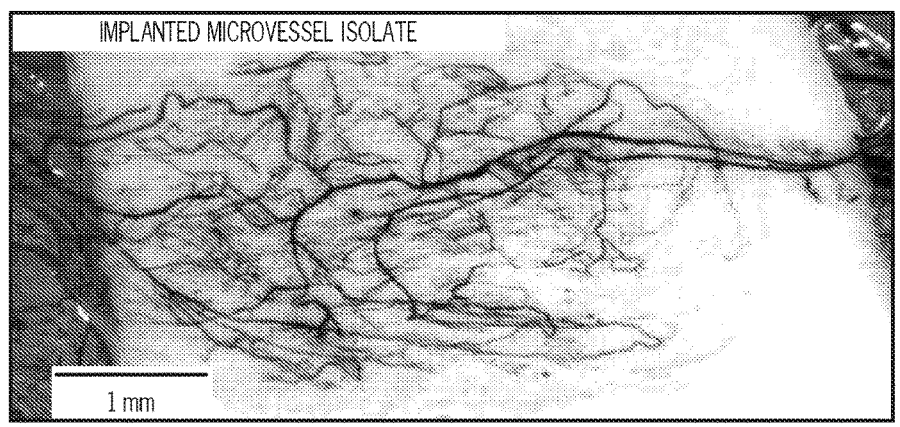

In specific embodiments, one or more IPMs and VIPMs (the terms module and device are used interchangeably when discussing IPM and VIPM embodiments) may be linked. In specific embodiments two or more modules/devices are linked synchronously in a closed-loop system. The devices may also be assembled in a linkage configuration based on investigative need, and may be linked to be perfusable in series or in parallel or in some combination thereof. In very specific embodiments, each device of a linkage comprises a living cell derived from a distinct tissue type. For example, FIGS. 9 and 10 exemplify a synchronous perfusable flow from a Liver IPM to a Kidney IPM.

In some specific embodiments, IPM and VIPM devices according to the invention may be designed and constructed from engineered-to-order (ETO) customer specifications of specific cell constructs or combinations of cell constructs or parallel and/or series integration of VIPM's with specific cell constructs. This can include, but is not limited to 3-D printed and assembled self-contained VIPM assemblies, VIPM assemblies incorporated into well-plates, and VIPM assemblies printed on microscope slides, etc. Downstream uses include, for example, drug testing and discovery applications.

According to other specific embodiments, the VIPM device may be provided as a kit of materials and an instructional protocol. The end user may have or acquire a 3-D printer and robotics assembly platform (a suitable platform is available from Advanced Solutions Life Sciences of Louisville, Ky. under the BioAssemblyBot™ brand) for manufacture and assembly.

Some embodiments of the present invention are directed to methods for manufacturing an in vitro microcirculation construct that is capable of adapting to hemodynamic and parenchymal cues. Generally, a network of vascular cell-lined channels in vascular communication with a "downstream" native, self-forming microvasculature in a microfluidic platform (FIG. 1) is constructed. A vascularized channel network serves to connect the external microfluidic perfusion support to the smaller caliber native microvasculature. This native microvasculature, derived from isolated, intact microvessels, generates a fully functioning and adaptable mature microcirculation.

According to some embodiments, the methods comprise: a) casting a network of channels on a polymerized matrix gel with a sacrificial material, said network cast to form at least one perfusion inlet port and inlet channel, and at least one perfusion outlet port and outlet channel, and one or more cross channels, each cross channel being in communication with both an inlet channel and an outlet channel; b) incorporating an isolate of intact native microvessels into a polymerizable matrix; c) distributing the polymerizable matrix from step b) over the network of cast channels and polymerizing the matrix to form a continuous polymerized gel matrix comprising both the network of cast channels and the intact native microvessels; d) incubating the gel matrix under conditions suitable to promote spontaneous growth of a neovasculature from the native microvessel isolate, said incubating optionally taking place before or after step c); e) flushing the sacrificial material from the cast network to yield a molded network of channels; f) lining the molded channels with endothelial cells to form a continuous network of endothelial cell-lined channels; and g) subjecting the network of endothelial cell-lined channels to perfusion with a perfusion fluid sufficient to induce endothelial sprouting from the one or more cross channels and inosculation between at least two sprouts and the neovasculature, thereby forming a stable adaptable microcirculation system. In mores specific embodiments, the methods further comprise maturing or adapting the microcirculation to a desired circulatory profile by modulating perfusion of a perfusion fluid through the microcirculation system. In specific embodiments, the casting step may be effectuated by 3-D bioprinting a bio-ink comprising a thermo-reversible hydrogel and the "distributing" step is effectuated by 3-D bioprinting a bio-ink comprising an isolate of intact native microvessels suspended in a gelable matrix. In certain embodiments, the subjecting step (g) comprises defining perfusion hemodynamics to provide a shear stress between the at least one inlet channel and the one or more cross channels sufficient to induce endothelial sprouting, for example, the provided shear stress may be greater than or equal to 10 dynes/cm$^2$.

In more specific embodiments, a sacrificial casting strategy involving the 3-D printing of a thermo-reversible hydrogel within a microfluidic chamber is utilized to form the microchannel network. Once printed, a prototype hydrogel network is flooded with un-polymerized collagen containing angiogenic, isolated microvessels able to spontaneously establish a neovasculature in vitro. Upon collagen polymerization, the printed hydrogel is flushed from the system leaving behind networked channels running through the microvessel-containing collagen. These channels are then lined with endothelial cells, which are induced to sprout into the surrounding collagen using defined perfusion conditions. The endothelial cell sprouts arising from the channels inosculate with the interconnected neovessels derived from the microvessels thereby establishing lumen continuity between the channels and the native neovasculature. Subsequent maturation of this immature neovasculature is driven by controlled pressure or flow across the system. It is this native microvessel-derived microvasculature, supplied by the channel network, which serves as a functional in vitro microcirculation.

The isolated microvessels spontaneously undergo angiogenesis to form neovessels which inosculate with each to form a neovascular network. Using the sacrificial casting approach in combination with 3-D printing, a network of endothelial cell-lined channels is established in close approximation to the microvessel-derived neovasculature in a microfluidic platform. Sprouts of endothelial cells lining microfluidic channels inosculate with the neighboring neovascular network within the gel matrix/collagen thereby forming contiguous perfusion pathways with the neovasculature. In specific embodiments, a blended thermo-reversible hydrogel (NIPAm microgel-doped Pluronic 127) with sufficient viscosity to hold shape when printed (i.e. be a gel), but that can then be dissolved (i.e. be a sol) for flushing out of the polymerized collagen, thereby leaving behind channels is utilized. Inosculation is promoted and guided by manipulating endothelial cell sprouting and angiogenesis in the channels and native microvascular networks, respectively.

Maturation of a newly formed microvasculature requires hemodynamic flow and pressure cues. Adaptation of the microcirculation in tissues to meet changing perfusion needs, via structural remodeling of individual microvessels, depends on these similar hemodynamic forces. The hemodynamic cues generated from perfusion of the constructed endothelial cell-lined channel network into the isolated microvessel-derived native microvasculature alter the topology of the functional microcirculation. An implication of this is that different perfusion protocols will induce structural adaptation resulting in microcirculations with different topologies and character. According to some embodiments, hemodynamic protocols within the microfluidic platform are modulated to promote maturation of the two-part vascular system. Experiments involve a combination of computational fluid mechanics modeling, real-time confocal imaging, vascular morphometry, and hemodynamic measurements to assess outcomes. A perfused in vitro microvascular network is established permitting exploration of hemodynamic-vessel network remodeling relationships in the in vitro microcirculation. Importantly, all of the cell types necessary to derive a mature microcirculation are present with the microvessel isolate.

Embodiments of the inventive isolated microvessel system enable an array of vascularizing strategies, and provide innovative solutions to scientific and translational challenges. To the best of the knowledge of the present investigators, this is the first bona fide in vitro microcirculation because it exhibits functional fidelity to a native physiological microcirculation.

Figure 2:
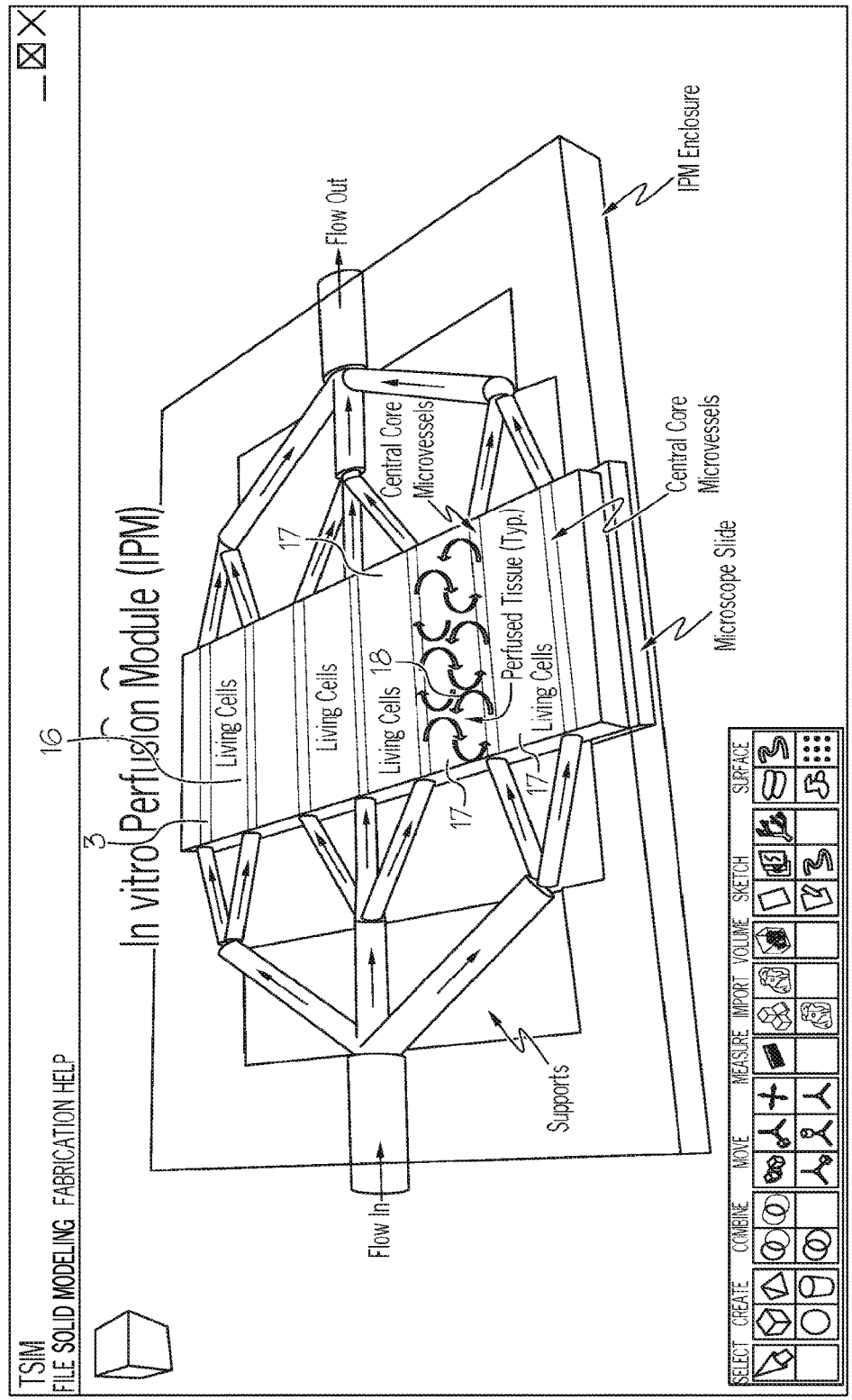
FIG. 2. User interface showing TSIM software-generated IPM populated with living cells and tissue in sections of gel matrix defined by cross-channels set up for 3-D printing on BioAssemblyBot™ platform.

Intact microvessels isolated from adipose (from rat, mouse, and human sources) have been utilized previously for investigations of angiogenesis, stromal cell and vascular precursor behavior, angiogenesis-tissue biomechanics, imaging modalities to assess neovascular behavior, post-angiogenesis microvascular maturation and patterning, and pre-clinical therapeutic applications. Importantly, the microvessel isolate, which is a heterogeneous collection of intact (i.e. all requisite vascular cells present in the native microvessels are retained) arterioles, capillaries and venules of varied diameters, spontaneously gives rise over approximately 7 days to a dense, interconnected network of immature neovessels with formed lumens (or neovasculature) when cultured in, for example, collagen gels (FIG. 2). The present inventors have previously shown that this same microvessel isolate in collagen progresses to form a mature microcirculation when implanted in vivo (FIG. 2). The neovessels spontaneously inosculate with other vasculatures (i.e. such as the host circulation), thereby providing perfusion of the implant. Surprisingly, the present inventors established that carefully modulated intravascular perfusion of these neovessels in culture promotes neovascular maturation and permits derivation of a true microcirculation in vitro.

Detailed protocols for forming user-defined geometries of perfusable endothelialized microvessel networks in hydrogel are set forth in Morgan et al. "Formation of microvascular networks in vitro" *Nature Protocols* Vol. 8, No. 9 2013, pp 1820-1836, the entire disclosure of which is incorporated herein by this reference.

3-D printing methods have evolved sufficiently to provide an ideal fabrication means for the requisite microstructures and precise placement demands of the inventive devices. Refinement of direct-write depositing of biocompatible hydrogels in defined 3-D structures has co-evolved with direct-write printer technology over the last ten years. Methods for fabricating channels via sacrificial casting by exploiting the precision and tolerance benefits and work flow potential of 3-D bioprinting platforms are known. (Miller et al. "Rapid casting of patterned vascular networks for perf usable engineered three-dimensional tissues." *Nature Materials* 11, 768-774 (2012), and Intl patent pub. No. WO2015069619 A1 to Lewis, J. et al.). According to the former, microchannels are pre-formed in a 3-D matrix by directly dispensing carbohydrate syrups that harden into a glass to form a cast of a desired microvascular network within a soft matrix. The glass is then dissolved and seeded with vascular cells forming a perfusable, vascular cell-lined, microchannel network. Once cast in the correct topology and surrounded by matrix, these materials are then flushed out of the system leaving behind open conduits which are subsequently sodded with vascular cells. One deficiency of this method, however, is the increased complexity of the work flow required by the necessity of heating the sugar syrup. This deficiency is shared by the latter methods, which rely on heating and light-curing methacrylated gelatin. Surprisingly, by utilizing Pluronic as the sacrificial material in, for example, the BioAssemblyBot® 3D printing system platform (available from Advanced Solutions Life Sciences, LLC of Louisville, Ky.), specialized heating and cooling tools on the printer were able to be eliminated. This, combined with using fibrin or collagen gels, enables printing sacrificial channels directly into a volume of unpolymerized matrix (which may also contain cells, etc), substantially reducing the complexity of the work flow and enabling a single flow from beginning to end of fabrication, or to any downstream endpoint including timed and controlled experimentation and generation/measurement/analysis of results with the fabricated IPM/VIPM device(s). In specific embodiments, implantable microvascular networks are formed using patterned Pluronic hydrogel placed in a collagen matrix as the channel-forming material.

According to some embodiments, 3-D printing solutions are used to fabricate endothelial cell-lined channels using a sacrificial casting approach as a means to connect the native microvessel-derived neovasculature to an external perfusion source.

The intravascular perfusion of the implanted neovasculature is critical to the subsequent maturation and formation of the in vitro microcirculation. Normally, as in the neovascular implants, the transition from angiogenesis to a functional microcirculation involves differentiation of neovessels into functional vessel types (i.e. arterioles, capillaries, and venules) and organization of these vessels into a vascular tree. The primary means by which network maturation/remodeling occurs is through structural adaptation of individual vessel segments. Hemodynamics plays a crucial role in driving these structural changes. Therefore, perfusion of the microvessel-derived neovasculature in the in vitro system matures the neovessels and neovascular network, simultaneously establishing a stable microcirculation for downstream uses.

Figure 3:
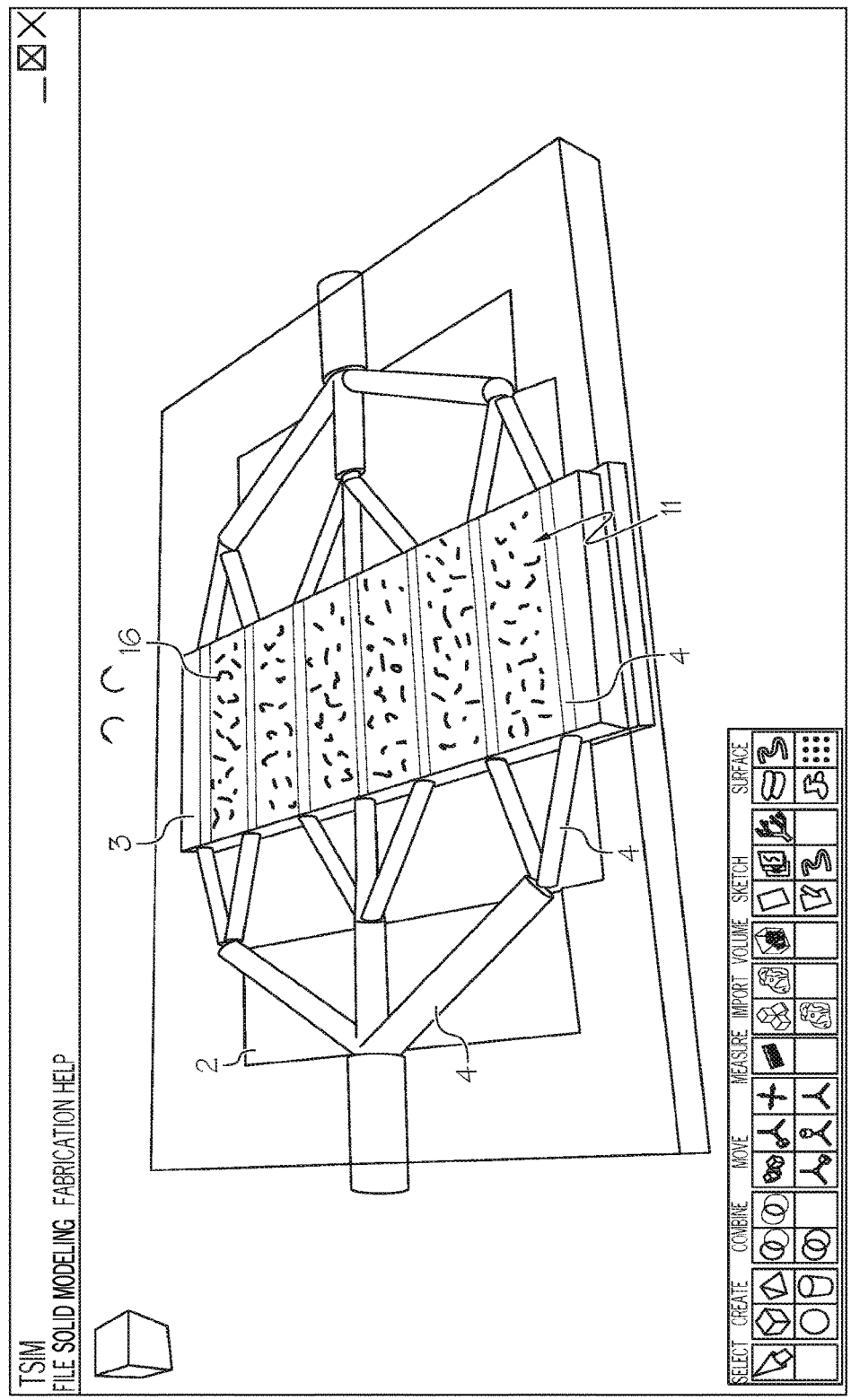
FIG. 3. User interface showing TSIM software-generated IPM showing intact microvessels integrated with the living cells in gel matrix set up for 3-D printing on BioAssemblyBot™ platform FIG. 4. Graphic depicting induced sprouting from endothelial lined cross-channels and microvessels.

Intact microvessels embedded in 3-D collagen I gels are capable of generating a new microcirculation when implanted in a living host by progressing through distinct vascular phases beginning with angiogenesis, leading to neovessel remodeling, followed by vessel and network maturation in a blood flow-dependent manner (FIG. 3). In culture, the isolated microvessels undergo angiogenesis to form a neovascular network (see FIG. 2) but do not mature further due to the absence of lumenal perfusion. Surprisingly, upon defined perfusion, the in vitro neovascular network matures and establishes a microcirculation in vitro just as it occurs in vivo. The average diameter of the neovessels is approximately 10 µm making it difficult to deliver fluid flow to the lumens of these neovessels directly from an external perfusion system. However, by progressively stepping down flow paths from the 1-2 millimeter diameter of external pump tubing to sub-millimeter diameters within the neovascularized collagen via a constructed network of endothelial cell-lined, microfluidic channels, it is possible to establish defined perfusion to the neovessels.

Figure 5:
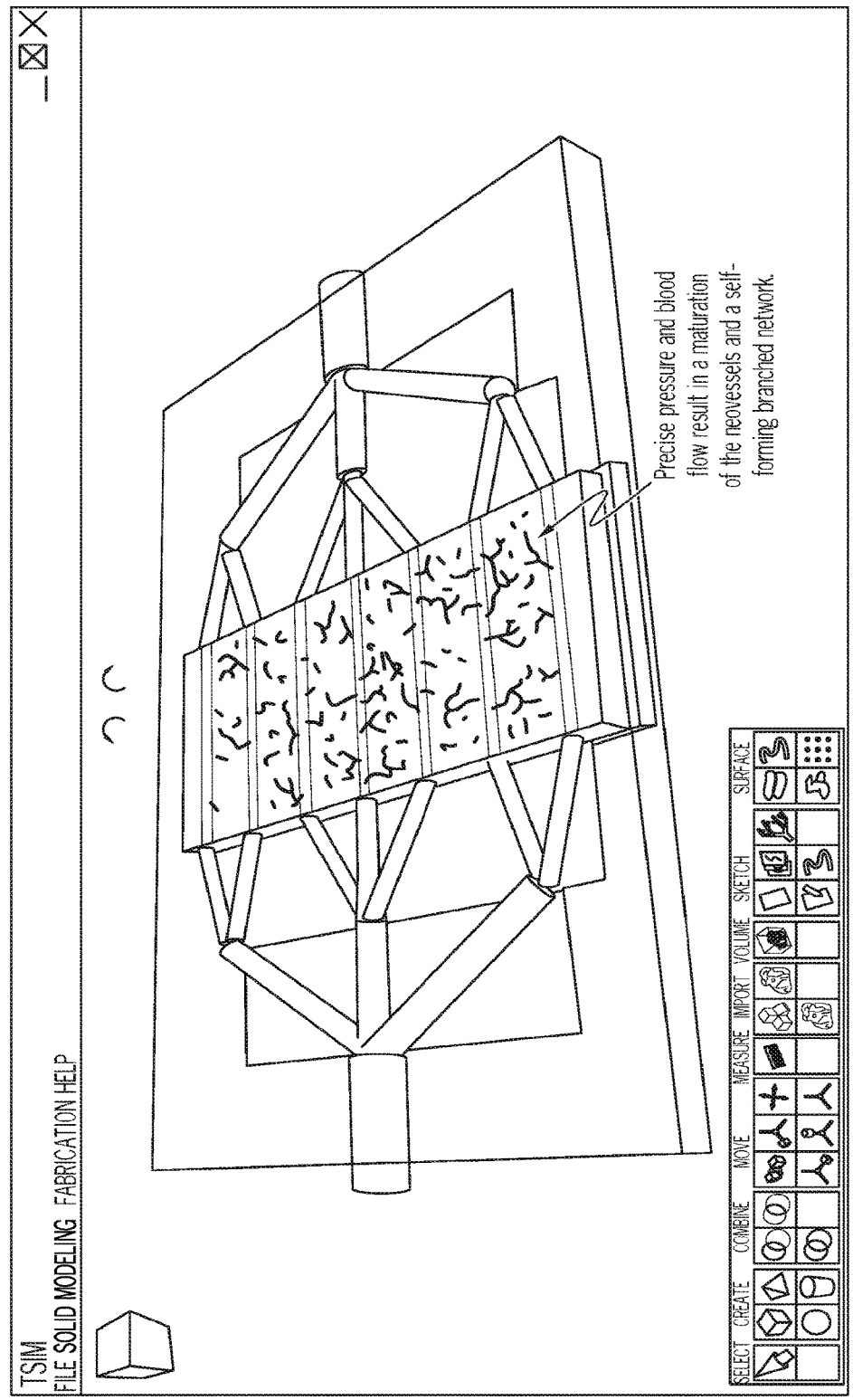
FIG. 5. Graphic demonstrating self-forming neovascularization under controlled perfusion conditions.

The endothelial cell-lined microfluidic channels are configured as an intermediate perfusion path to the native microvessel-derived neovasculature (see FIG. 1). The channel network may be configured in many alternative designs. It may be constructed as a hierarchical tree with each branch order reducing in diameter from 2 mm to a final channel diameter of 200 µm. This arrangement is duplicated such that there is an in-flow side leading to a "distal" segment of channels where diameters are small and flows are low draining into an out-flow side. The step-wise reduction (and corresponding increase on the outflow side) in channel diameter is based on three considerations: 1) the smallest channel segment, at ~200 µm in diameter, is analogous to feed arteries in a native vascular tree, 2) for typical microfluidic flow rates, there will be ~10 dynes/cm$^2$ at the smallest segment) the diameter of each branch is ~⅗ that of the parent channel (again, analogous to native vascular trees). It is desirable for the channels in the segment intended to produce endothelial cell sprouts that will inosculate with native neovessels (the 200 µm channels) to be small enough in caliber to not generate too large of a diameter difference (and therefore a pressure drop) between the channel and the neovessels connected to it. Also, it needs to be of a diameter that will generate a fluid shear stress on the endothelial cells lining the channels sufficient to induce sprouting. In a similar setup in which endothelial cell lined a collagen gel surface, 10 dynes/cm$^2$ of wall shear stress across the endothelium induced the endothelial cells to sprout and invade the collagen. An algorithm for generating a 3-D model of a channel network by simply entering these initial boundary parameters is developed. This model is then used to instruct a direct-write printer to fabricate the network (FIG. 5).

According to specific embodiments, the inlet channel and the at least one cross channel have a cross-sectional diameter ratio between about 1.1:1 and about 5:1. The network may be constructed with at least two cross channels having different cross-sectional diameters such that a hemodynamic gradient is formed between the cross channels upon perfusion. In other specific embodiments, the configuration of the network is intended to duplicate physiological resistance patterns across a microcirculation.

The following Examples illustrate specific features and aspects of embodiments of the invention and should not be construed as limiting the full scope of the invention as defined by the claims.

EXAMPLES

The following examples describe fabrication of a perfused, native microvasculature in vitro.

Example 1

This example illustrates development of a system of endothelial cell-lined channels connected to a network of neovessels derived from native microvessels in a microfluidic chamber. Although a very specific printed channel network configuration is illustrated, alternative branching designs may be employed for specific applications. Further, designs incorporating rounded channel junctures and unequal cross channels, to more closely mimic physiological vasculature are contemplated. Several academic publications are cited to provide protocol details and the disclosures of all cited publications are incorporated herein by this reference. In some instances, alternative aspects are noted where substitution has been empirically verified with predictable results. Expressed alternatives should not, however, be considered exhaustive of equivalents.

1. Within a well of a 24-well plate, the desired channel network is prototyped in the ASLS TSIM™ software environment with each branch order having a different diameter. In this specific example, a "ladder" design (FIG. 5) in which supply channels (~400 µm OD) support perfusion of smaller, "distal" channels (~200 µm) intended to enable inosculation with the surrounding neovasculature is printed.

Figure 6:
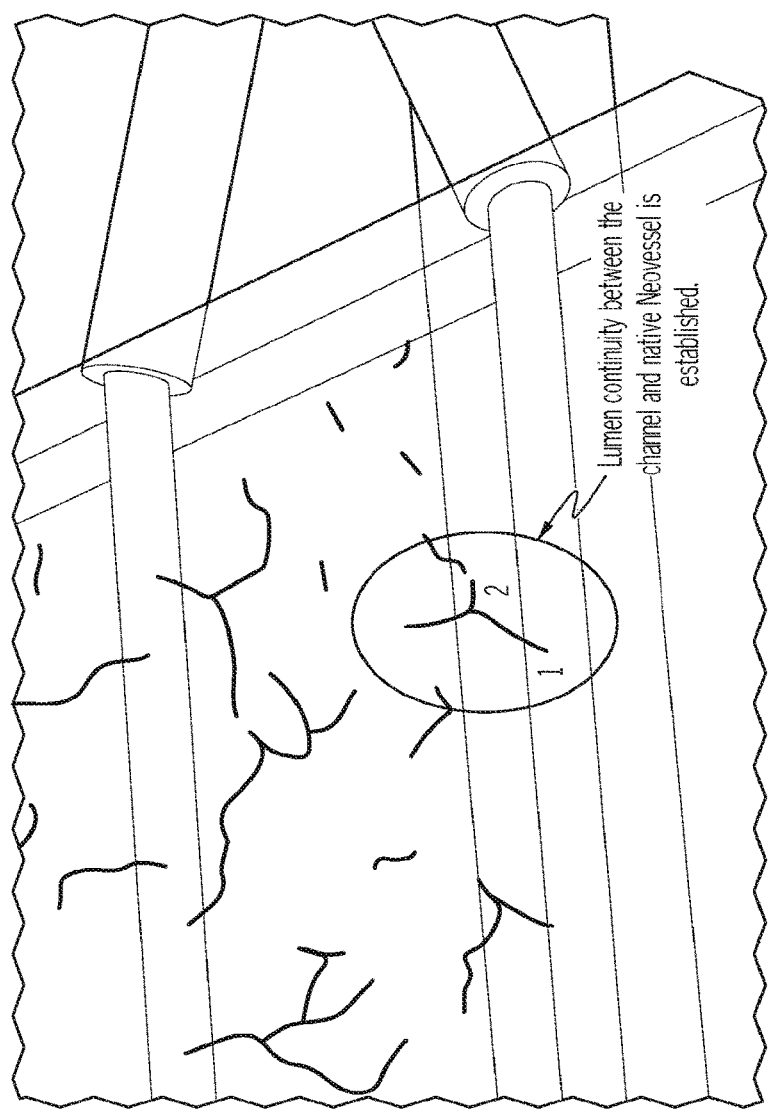
FIG. 6. Graphic illustrating establishment of lumen continuity between endothelial cell-lined channel and microvessel with inosculation between sprouts.
Figure 7:
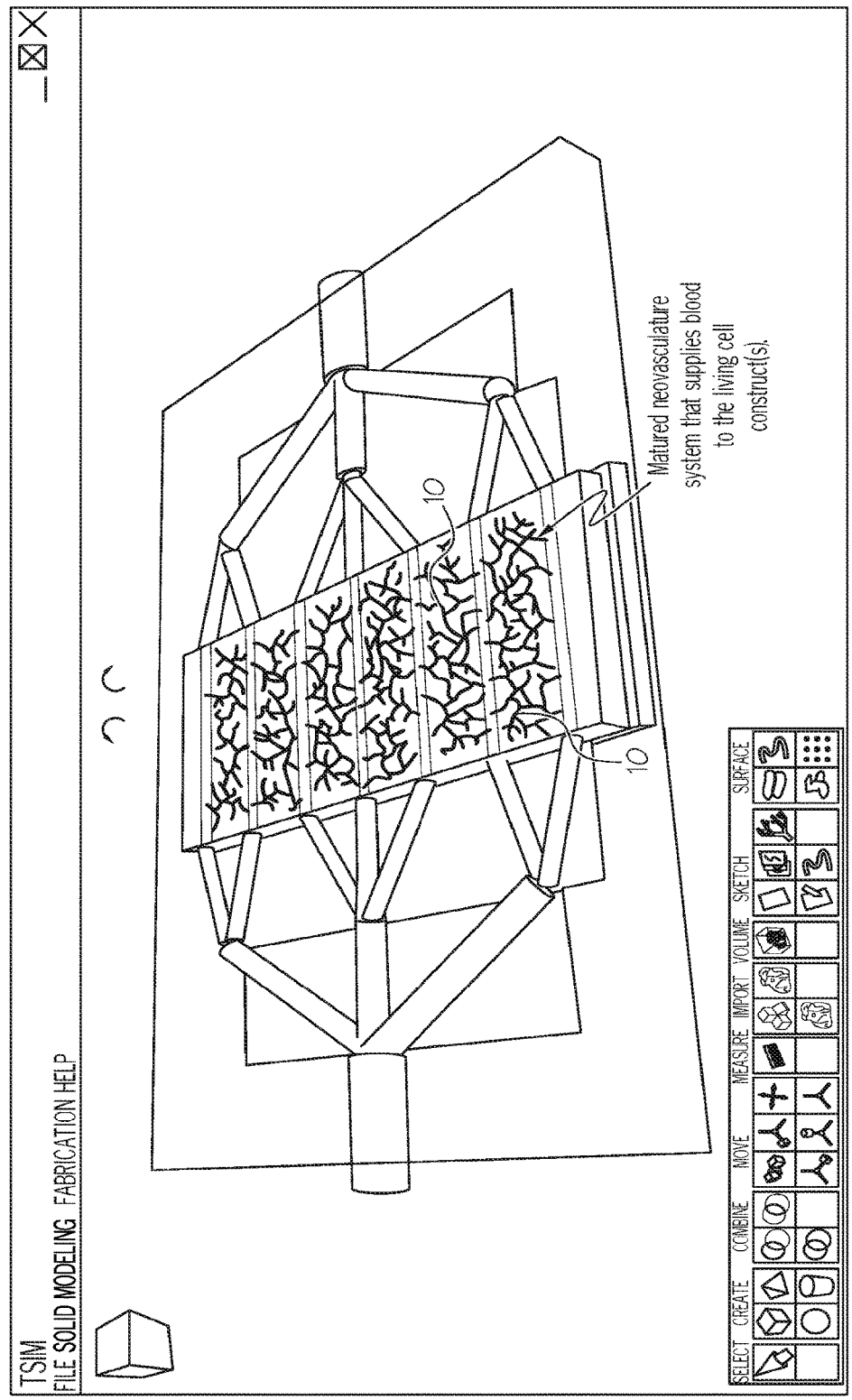
FIG. 7. Illustration of matured neovasculature (microcirculation) that provides perfusion fluid to living cells in gel matrix.
Figure 8:
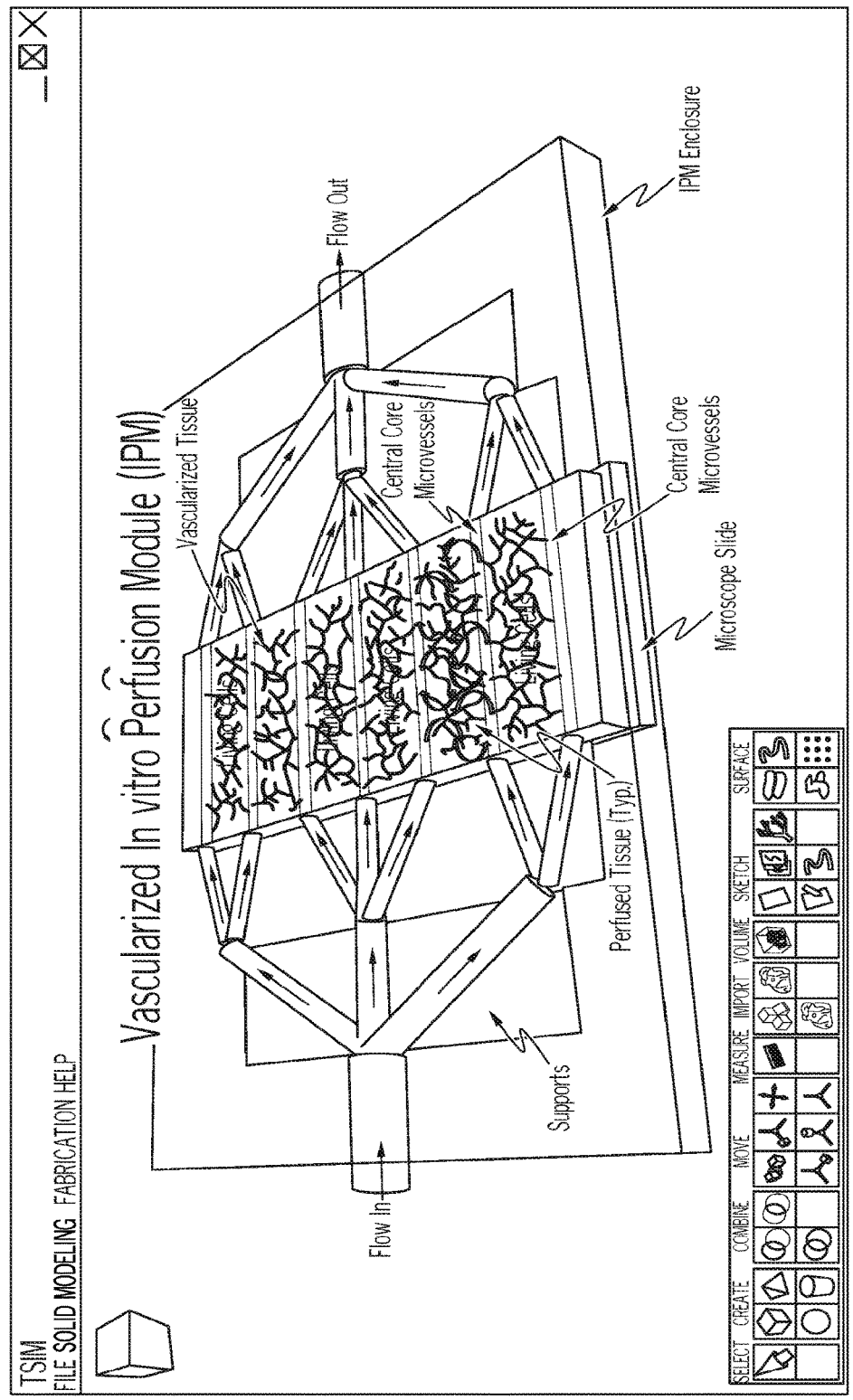
FIG. 8. User interface depiction of a 3-D printable VIPM embodiment depicting flow of perfusion fluid, adaptable neovasculature in gel matrix sections populated with living cells and/or tissue types.

On a bed of polymerized collagen (or fibrin; microvessels grow well in either 3-D matrix), the channel network with the desired reservoirs/ports are printed at room temperature using different cartridges containing thermo-reversible Pluronic F127 in PBS (or a high-density suspension of soft ULC NIPAm microgels; Pluronic (co-block polymer of polypropylene glycol and polyethylene glycol) is a gel at room and warmer temperatures and a sol below 10-12° C., whereas ULC pNIPAm microgels (ultra-low crosslinked poly(N-isopropylacrylamide) are gel-like (swollen) at room temperature and below but are suspended nanoparticles (de-swollen, sol-like) at or above 33° C. Importantly, both are gels at the temperatures at printing conditions (room temperature) and have sufficient viscosity to hold shape when printed) fitted with needles sized to match the desired diameter (using an integrated proprietary software/printing/robotics platform available from Advanced Solutions Life Sciences, Louisville, Ky., which is capable of utilizing multiple cartridges in one print). Cold, pH neutralized, un-polymerized collagen (3 mg/ml) (or room temperature fibrinogen/thrombin solution (Stabenfeldt S E et al. *Biomaterials*. 2012; 33(2):535-44) containing approximately 40,000 human microvessels/ml prepared as previously described using serum free medium containing 10 ng/ml VEGF (Chang et al. *Tissue Eng* Part A. 2010; 16(3):795-805; Nunes et al. *Microcirculation*. 2010; 17(7):557-67; Nunes et al. *Microvasc Res*. 2010; 79(1):10-20; Edgar et al. PLoS One. 2014; 9(1):e85178; Nunes et al. PLoS One. 2011; 6(11):e27332), is dispensed over the printed channel network using the 3-D printer with the intent of covering the segment of the channel network containing the narrowest channels (FIG. 6; also, the red channels in the CAD design and the blue channels in the printed network of FIG. 5). This placement brings growing neovessels and sprouting endothelial cells in close approximation to each other. The remainder of the network is covered with microvessel-free collagen.

2. The entire system is heated in-place to 37° C. for 30+ minutes to polymerize the collagen (or fibrin). With Pluronic channels, this firms them up making these more gel-like. With the NIPAm microgels this de-swelling will them making them more fluid and therefore easy to flush from the system. With the Pluronic/collagen combination, they will need to be placed and flushed at 4° C. (cooling the microvessels does not injure them).
3. Once polymerized, the microfluidic chamber (defined by the well walls) is fitted with a customized lid (constructed previously from PDMS) containing access ports aligned with each of the Pluronic ports of the channel network.
4. Perfusion tubing is inserted, and sealed with the lid. The stage is then cooled to 4° C. for 15 minutes to solubilize the Pluronic gel (this does not harm the microvessels) which is then flushed from the system by pushing Hank's balanced salt solution (HBSS) through one port and out the other as described by others for Pluronic channels in collagen (Hooper et al. *Tissue Eng Part A*. 2014.
5. Once flushed, the channel walls are endothelialized by perfusing through the now patent channels a suspension of $5\times10^6$/ml of low-middle passaged HUVECs (or microvascular endothelial cells) in M199 plus 20% fbs and endothelial cell growth supplement (ECGS). Approximately 20 μL of the cell suspension is delivered to the channel network through one port and into the network via microfluidic forces.
6. The system is then incubated for 60 min. at 37° C. to promote EC attachment in a $CO_2$ incubator followed by culturing with perfusion through the channels at low flow rates (producing a wall shear stress of ~0/1 dynes/cm$^2$) with a serum-free medium comprised of M199 containing 50 μg/ml ascorbic acid, 2 mg/ml bovine serum albumin (BSA), 20 ng/ml human holo-transferrin, 20 ng/ml insulin, 17.1 ng/ml sodium oleate, and 0.02 ng/ml sodium selenite (Hooper et al. Tissue Eng. Part A, 2014) for 3 days to establish a complete monolayer on the channel walls.
7. On day 4, 1 μM S1P is added to the perfusate and flow rates are raised to produce 10 dynes/cm$^2$ at the narrowest channel segments to induce EC sprouting (Kang et al. *Am J Physiol Heart Circ Physiol*. 2008; 295(5):H2087-H97.
8. At select times, the system is perfused with UEA-1 lectin coupled to FITC to label all endothelial cells, followed by perfusion with 2% paraformaldehyde/PBS to fix the system for characterization.

A range of Pluronic F127 hydrogels (15, 20, and 28% w/v) is considered for formation stiff channel casts during printing and collagen polymerization with good flushing characteristics upon the appropriate temperature change. The S1P and 10 dynes/cm$^2$ induces endothelial cell sprouting from the channel walls. Neovessels spontaneously sprout and grow from the isolated microvessels in minimal media. In some embodiments, angiogenic factor-enriched media is used to promote this. We have demonstrated previously that perfusion of culture media through just the channels is sufficient to support angiogenesis by the microvessels (Chang et al. *Tissue Eng* Part A. 2010; 16(3):795-805). HUVECs are transfected with a constitutive RFP reporter cassette using lentivirus. Microvessels are isolated from discarded human adipose lipoaspirates following elective liposuction surgery. A CorSolutions™ microfluidics pump is used to provide continuous flow through the chamber with defined flow rates. The ASLS 3-D printer (Louisville, Ky.) is capable of printing lines of materials that are as narrow as 50 microns wide and 20 microns apart without having the materials run together. The entire system is designed to enable visualization of all aspects via phase or epifluorescence microscopy with an inverted microscope.

Assessment and evaluation The printed channel casts are visible by phase contrast microscopy or, if preferred, can be doped with a food coloring or a fluorescent dye. The endothelialized channels and neovasculature is visualized by epifluorescence and confocal microscopy using the reporters over the course of 10 days. Connectivity of flow paths is assessed using fluorescent (far-red) dextran (3 million MW) delivered via the perfusion system and imaged as above. At specific time-points, whole fixed VIPMs are examined via confocal microscopy through the University of Louisville's microscopy core. Total channel and neovascular length densities are measured from stitched, rendered confocal image stacks acquired at 4, 7 or 10 days after establishing the endothelial cell coverage of the channels to determine any changes in endothelialization and the extent of neovascular growth. In addition, the number of red (RFP)/green (UEA-1) EC-neovessel junctions as a function of neovessel length density is counted to assess the frequency of inosculation events.

Results. An in vitro perfused neovasculature is generated. Microvessels isolated from adipose and microvessel assay kits are available from Angiomics, Inc. Angiomics, Inc. obtains de-identified, discarded liposuction adipose from local plastic surgeons via an agreement with the University of Louisville. Preliminary studies indicate numerous inosculation events between neovessel ends, and a relatively low number of channel EC-neovessel connections. However, we determined that only a few inosculation events are necessary to drive maturation of the neovasculature. This is because the angiogenic neovessels themselves already interconnected forming a network of contiguous lumen. Thus, once there is perfusion into one or two segments of the neovasculature, flow is immediately distributed throughout the neovasculature and maturation is initiated. Density of seeded microvessels and addition of angiogenic factors to the perfusion media may be varied to induce greater sprouting where necessary. Based on initial results, different channel configurations influence inosculation probabilities and increasing the number of cross-channels (distal channels) increases inosculation probabilities. Flow mechanics may be optimized by configuration of the in-flow and out-flow path designs. An optimal configuration is empirically determined. The ASLS proprietary integrated software/printing/robotics platform enables rapid prototyping and testing. Alternative gels and gel blends are being explored. According to some embodiments, a gelatin/Pluronic containing no more than 10% Pluronic is utilized. In other embodiments, the gel comprises a NIPAM microgel-doped Pluronic (available from GE Healthcare Life Sciences). In very specific embodiments, the gel comprises a soft ULC NIPAm microgel (ultra-low crosslinked poly(N-isopropylacrylamide nanoparticles) which are gel-like (swollen) at room temperature and below but are suspended nanoparticles (de-swollen, sol-like) at or above 33° C. (Brown et al. LID-10.1038/nmat4066 [doi](1476-1122 (Electronic) and Gan et al. (0002-7863 (In print)). Importantly, both are gels at room temperature and have sufficient viscosity to hold shape when printed.

Example 2

This example illustrates derivation of a microcirculation by maturing the connected neovasculature via defined perfusion.

The neovasculature is flow-conditioned once connected to the EC-lined channels. The regimen used to establish the neovasculature is continued for an additional 2 weeks. The initial perfusion protocol establishes wall shear stresses of 10 dynes/cm$^2$ in the "distal" part of the channel network, however the evolution of the neovasculature is monitored, permitting accommodating changes to be made based on the extent of maturation (assessed by changes in segment diameters across the network), in the pressure drop and/or flow rates through the system to influence neovessel structural adaptation. A perfusion protocol sufficient to derive a mature microcirculation is determined. The established mature microcirculation is quantified. Hemodynamic variables are systematically changed and coupled with assessments to define microvascular network topologies specific to a given set of perfusion parameters.

Example 3

The following example illustrates perfusion-driven inosculation between two derived neovasculatures.

Figure 4:
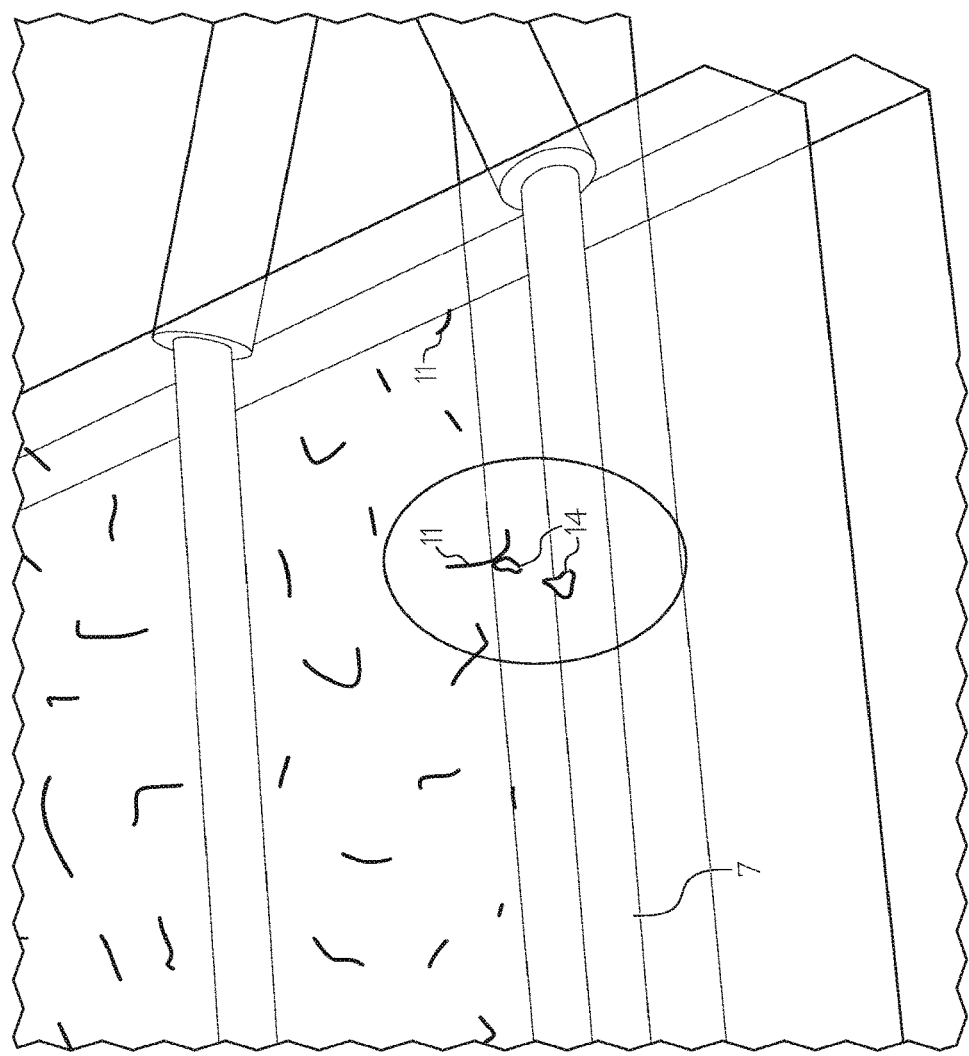

Green endothelial cells (from a tie2:GFP transgenic mouse) were co-cultured with red neovessels derived from microvessels isolated from a RFP-expressing transgenic mouse. While not frequent, connected red and green neovessels were observed demonstrating inosculation between the two-derived neovasculatures (FIG. 4a,b). Initially, endothelial cells lining the channels are induced to sprout into the surrounding collagen matrix becoming available for inosculation (FIG. 4c). Importantly, because the isolated microvessels maintain lumens following the isolation, the neovessels that grow out from these "parent" microvessels also have lumens. Thus, by joining the channel network and neovasculature (joined by endothelial cell connections) to an external pump, it is possible to perfuse the neovasculature thereby maturing it into a functional microcirculation.

Assessment and evaluation Image data is used to determine topology (microvessel diameters and arrangement) of the microvasculatures (these trees are small, limiting the time and effort to perform this mapping). An examination of red/green junctions within the microvasculature determines the extent and site (within the channel network) of channel-vessel inosculations. Perfusion paths through the tree are assessed using fluorescent microsphere tracers ranging in size from 5 µm to 20 µm in diameter (each of a different color) to map perfusion through the different segments of the microvasculature. At the end of the culture period, the networks are collected and en bloc immunostaining is performed for the presence of mural cells (β-actin) and EC-EC junctions (VE-Cadherin) using standard, published methods (Nunes et al. *Microvasc Res.* 2010; 79(1):10-20) as indicators of maturity.

Results The significant impact of hemodynamic forces on microcirculation topologies is well known (LeBlanc et al. *Microcirculation.* 2012; 19(8):676-95). Topologies of the in vitro microcirculation change in response to changes in pressure and flows.

What is claimed is:

1. A vascularized in vitro perfusion device comprising an adaptable microcirculation, said device comprising:
   a supporting structure comprising a gel matrix,
   a fabricated network of microfluidic endothelial cell-lined channels, said fabricated network comprising an inlet channel, an outlet channel, and at least one cross channel connecting the inlet channel to the outlet channel, said cross channel positioned at least partially within the gel matrix,
   an inlet port in fluid communication with the fabricated network, and an outlet port in fluid communication with the fabricated network, and
   a neovasculature, said neovasculature being derived from intact native microvessels incorporated into the gel matrix and subject to maturing conditions comprising endothelial sprouting and an inosculation between at least two endothelial sprouts respectively derived from the at least one cross channel of the fabricated network and the neovasculature to form a lumen connection therebetween, said neovasculature thus in lumen continuity with said at least one cross channel through the inosculation,
   wherein the fabricated network is in vascular communication and lumen continuity with the neovasculature to form an adaptable microcirculation.

2. The device according to claim 1, further comprising an enclosure comprising a housing.

3. The device according to claim 2, wherein the housing comprises a biocompatible plastic polymer selected from acrylic, styrene and carbonate polymers.

4. The device according to claim 2, wherein the at least one inlet port and at least one outlet port are accessed exterior to the enclosure.

5. The device according to claim 1, wherein the gel matrix is selected from a collagen gel, a fibrin gel, and combinations thereof.

6. The device according to claim 1, wherein the intact native microvessels are derived from adipose tissue.

7. The device according to claim 1, wherein the vascular communication is formed from perfusion-driven sprouting from the fabricated network of endothelial cell-lined channels, and inosculation between at least two sprouts and the neovasculature.

8. The device according to claim 1, wherein the inlet channel and the at least one cross channel have a cross-sectional diameter ratio between about 1.1:1 and about 5:1.

9. The device according to claim 8, comprising at least two cross channels having different cross-sectional diameters such that a hemodynamic gradient is formed between the cross channels upon perfusion.

10. The device according to claim 1, further comprising an external perfusion control system in operational communication with the fabricated network through the inlet port.

11. The device according to claim 1, wherein adaptable comprises an ability to undergo vascular differentiation and/or positive vascular remodeling in response to at least one perfusion-driven hemodynamic force or stimuli.

12. The device according to claim 11, wherein the at least one hemodynamic force is one or more of intravascular pressure and shear stress.

13. The device according to claim 1, further comprising living cells, said cells populating the gel matrix and being derived from one or more tissue types.

14. The device according to claim 13, wherein the cells are all from the same tissue type.

15. The device according to claim 13, wherein the gel matrix comprises at least two sections and each section is populated with cells from a distinct tissue type.

16. The device according to claim 13, wherein the living cells comprise human cells.

17. The device according to claim 13, wherein the living cells are selected from one or more of normal cells, diseased cells, stem cells, endothelial cells, stromal cells, epithelial cells, neuronal cells, connective cells, myocardial cells, hepatocytes, renal cells, tumor cells, liver cells, pancreatic cells, muscle cells, brain cells, kidney cells, and patient-specific cells.

18. The device according to claim 13, wherein adaptable comprises an ability to undergo vascular remodeling in response to at least one cue provided by the living cells.

19. The device according to claim 18, wherein the at least one cue is provided by the living cells in response to an agent delivered by perfusion.

20. The device according to claim 1, wherein the vascular communication is formed from one of perfusion-driven sprouting, cell-driven sprouting, growth factor-driven sprouting, and matrix driven-sprouting from the fabricated network of endothelial cell-lined channels, and inosculation between at least two sprouts and the neovasculature.

* * * * *